US006958237B2

(12) United States Patent
Frey et al.

(10) Patent No.: US 6,958,237 B2
(45) Date of Patent: Oct. 25, 2005

(54) HIGHLY INFECTIOUS RUBELLA VIRUS DNA CONSTRUCTS AND METHODS OF PRODUCTION

(75) Inventors: Teryl K. Frey, Atlanta, GA (US); Konstantin V. Pugachev, Natick, MA (US); Emily S. Abernathy, Atlanta, GA (US); Wen-Pin Tzeng, Duluth, GA (US)

(73) Assignee: Georgia State Univesity Research Foundation, Inc., Atlanta, GA (US)

( * ) Notice: Subject to any disclaimer, the term of this patent is extended or adjusted under 35 U.S.C. 154(b) by 0 days.

(21) Appl. No.: 10/271,311

(22) Filed: Oct. 15, 2002

(65) Prior Publication Data

US 2003/0130498 A1 Jul. 10, 2003

Related U.S. Application Data

(63) Continuation-in-part of application No. 09/557,232, filed on Apr. 24, 2000, now abandoned, which is a continuation of application No. 08/999,733, filed on Sep. 2, 1997, now Pat. No. 6,054,573, which is a continuation-in-part of application No. 08/459,041, filed on Jun. 2, 1995, now Pat. No. 5,663,065, which is a continuation-in-part of application No. 08/093,453, filed on Jul. 19, 1993, now Pat. No. 5,439,814, which is a continuation of application No. 07/722,334, filed on Jun. 28, 1991, now abandoned.
(60) Provisional application No. 60/329,686, filed on Oct. 15, 2001.

(51) Int. Cl.$^7$ .............................. C12N 7/01; C12N 15/86

(52) U.S. Cl. ................................ 435/320.1; 435/91.33; 435/91.4; 435/235.1; 424/199.1

(58) Field of Search ............................. 435/91.33, 91.4, 435/320.1, 235.1, 471, 472, 456; 424/199.1

(56) References Cited

U.S. PATENT DOCUMENTS

| | | | | |
|---|---|---|---|---|
| 5,439,814 A | * | 8/1995 | Frey et al. ................... | 435/455 |
| 5,663,065 A | | 9/1997 | Frey et al. | |
| 5,925,565 A | | 7/1999 | Berlioz et al. | |
| 6,054,573 A | | 4/2000 | Frey et al. | |

OTHER PUBLICATIONS

Frolov et al (PNAS 93:11371–11377, 1996).*
Pugachev et al (Journal of Virology 74:10811–10815, Nov. 2000).*
Knight (Molecular and Cellular Neuroscience 14:486–505, 1999).*
Ahlquist, P., et al., "Nucleotide Sequence of the Brome Mosaic Virus Genome and its Implications for Viral Replication", *J. Mol. Biol.*, vol. 172, No. 4, pp 369–383 (1984).
Ahlquist, P., et al., "cDNA Cloning and In Vitro Transcription of the Complete Brome Mosaic Virus Genome", *Mol. Cell. Biol.*, vol. 4, No. 12, pp 2876–2882 (1984).

Barnes, W.M., et al., "PCR Amplification of up to 35–kb DNA with High Fidelity and High Yield form Lambda Bacteriophage Templates", *Proc. Natl. Acad. Sci. USA*, vol. 91, No. 6, pp 2216–2220 (1994).
Boyer, J.C., et al., "Infectious Transcripts and cDNA Clones of RNA Viruses", *Virology*, vol. 198, pp 415–426 (1994).
Bredenbeek, P., et al., "Sindbis Virus Expression Vectors: Packaging of RNA Replicons by Using Defective Helper RNA's", *J. Virol.*, vol. 67, No. 11, pp. 6439–6446 (1993). (Abstract Only).
Callahan, P.L., et al., "Molecular Cloning and Complete Sequence Determination of RNA Genome of Human Rhinovirus Type 14", *Proc. Natl. Acad. Sci. USA*, vol. 82, No. 3, pp 732–736 (1985).
Chantler, J.K., et al., "Characterization of Rubella Virus Strain Differences Associated With Attenuation", *Intervirology*, vol. 36, No. 4, pp 225–236 (1993).
Chen, M., et al., "Mutagenic Analysis of the 3' cis–Acting Elements of the Rubella Virus Genome", *J. Virol.*, vol. 73, No. 4, pp 3386–3403 (1999).
Cheng, S., et al., "Effective Amplification of Long Targets from Cloned Inserts and Human Genomic DNA", *Proc. Natl. Acad. Sci. USA*, vol. 91, No. 12, pp 5695–5699 (1994).
Clarke, D.M., et al., Nucleotide Sequence and In Vitro Expression of Rubella Virus 24S Subgenomic Messenger RNA Encoding the Structural Proteins E1, and E2 and C, *Nucleic Acids Res.*, vol. 15, No. 7, pp 3041–3057 (1987).
Cotlier, E., et al., Pathogenic Effects of Rubella Virus on Embryos and Newborn Rats, *Nature*, vol. 217, No. 123, pp 38–40 (1968).
Cunningham, A.L., et al., Persistent Rubella Virus Infection of Human Synovial Cells Cultured in Vitro, *J. Infect. Dis.*, vol. 151, No. 4, pp 638–645 (1985).
Davis, et al., "In Vitro Synthesis of Infectious Venezuelan Equine Encephalitis Virus RNA from a cDNA clone: Analysis of a Viable Deletion Mutant", *Virology*, vol. 171, No. 1, pp 189–204 (1989).

(Continued)

*Primary Examiner*—Mary E. Mosher
(74) *Attorney, Agent, or Firm*—Kilpatrick Stockton LLP

(57) ABSTRACT

Highly infectious rubella virus cDNA clones derived from infectious cDNA clone having a low specific infectivity and methods of obtaining highly infectious rubella virus cDNA clones. Togavirus expression vectors of improved stability for the expression of live, attenuated togavirus and a foreign gene, based on the nucleic acid sequence of an infectious rubella virus clone and contain a togavirus non-structural protein open reading frame; an expression element for expression of a foreign gene; a foreign gene or a multiple cloning site for insertion of a foreign gene; an expression element for the expression of the live, attenuated togavirus; and a togavirus structural protein open reading frame. The expression element is either a subgenomic promoter or an internal ribosome entry site (IRES). Administration of the vector as an immunization agents is useful for the induction of immuity against the togavirus, the foreign gene, or both.

5 Claims, 7 Drawing Sheets

OTHER PUBLICATIONS

Dominguez, et al., "Sequence of the Genome RNA of Rubella Virus: Evidence for Genetic Rearrangement During Togavirus Evolution", *Virology,* vol. 177, No. 1, pp 225–238 (1990).

Forng, R.Y., et al., "Identification of the Rubella Virus Nonstructural Proteins", *Virology,* vol. 206, No. 2, pp 843–854 (1995).

Frenkel, L.M., et al., "A Search for Persistent Measles, Mumps, and Rubella Vaccine Virus in Children with Human Immunodeficiency Virus Type 1 Infection", *Arch. Pediatr. Adolesc. Med.,* vol. 148, No. 1, pp 57–60 (1994).

Frey, T.K., et al., "Molecular Cloning and Sequencing of the Region of the Rubella Virus Genome Coding for Glycoprotein E1", *Virology,* vol. 154, No. 1, pp 228–232 (1986).

Frey, T.K., et al., "Sequence of the Region Coding for Virion Proteins C and E2 and the Carboxy Terminus of the Nonstructural Proteins of Rubella Virus: Comparison With Alphaviruses", *Gene.,* vol. 62, No. 1, pp 85–99 (1988).

Frey, T.K., et al., "Identification of the 5' end of the Rubella Virus Subgeomic RNA", *Virology,* vol. 168, No. 1, pp 191–194 (1989).

Frey, T.K., et al., "Identification of Strain–Specific Nucleotide Sequences in the RA 27/3 Rubella Virus Vaccine", *J. Infect. Dis.,* vol. 168, No. 4, pp 854–864 (1993).

Frey, T.K., "Molecular Biology of Rubella Virus", *Adv. Virus Res.,* vol. 44, pp 69–160 (1994).

Geiger, R., et al., "Persistent Rubella Infection After Erroneous Vaccination in an Immunocomprised Patient With Acute Lymphoblastic Leukemia in Remission", *J. Med. Virol.,* vol. 47, No. 4, pp 442–444 (1995).

Green, K.Y., et al., "Rubella Virus Antigens: Localization of Epitopes Involved in Hemagglutination and Neutralization by Using Monoclonal Antibodies", *J. Virol.,* vol. 57, No. 3, pp 893–898 (1986).

Hobman, T.C., et al., "Assembly of Rubella Virus Structural Proteins into Virus–Like Particles in Transfected Cells", *Virology,* vol. 202, No. 2, pp 574–585 (1994).

Hovi, T., et al., "Infectivity and Some Physicochemical Characteristics of Rubella Virus Ribonucleic Acid", *Virology,* vol. 42, No. 1, pp 1–8 (1970).

Kono, R., et al., "Experimental Vertical Transmission of Rubella Virus in Rabbits", *Lancet.,* vol. 1, No. 7590, pp 343–347 (1969).

Liljestrom, P., et al., "A New Generation of Animal Cell Expression Vectors Based on the Semliki Forest Virus Replicon", *Bio/Technology,* vol. 9, No. 12, pp. 1356–1361 (1991). (Abstract Only).

London, W.T., et al., *Symp. Series Immunobiol. Standard.,* vol. 11, pp 121–124 (1969).

London, W. T., et al., "Concentration of Rubella Virus Antigen in Chondrocytes of Congenitally Infected Rabbits", *Nature,* vol. 226, No. 241, pp 172–173 (1970).

Mauracher, C.A., et al., "Selective Tolerance to the E1 Protein of Rubella Virus in Congenital Rubella Syndrome", *J. Immunol.,* vol. 151, No. 4, pp 2041–2049 (1993).

Marr, L.D., et al., "Efficient in Vitro Translation and Processing of the Rubella Virus Structural Proteins in the Presence of Microsomes", *Virology,* vol. 180, No. 1, pp 400–405 (1991).

Mitchell, L.A., et al., "Chronic Rubella Vaccine–Associated Arthropathy", *Arch. Intern. Med.,* vol. 153, No. 19, pp 2268–2274 (1993).

Mizutani, S., et al., "In Vitro Synthesis of an Infectious RNA from cDNA Clones of Human Rhinovirus Type 14", *J. Virol.,* vol. 56, No. 2, pp 628–632 (1985).

Nakhasi, H.L., et al., "Rubella Virus cDNA. Sequence and Expression of E1 Envelope Protein", *J. Biol. Chem.,* vol. 261, No. 35, pp 16616–16621 (1986).

Niesters, H.G., et al., "Defined Mutations in the 5' Nontranslated Sequence of Sindbis Virus RNA", *J. Virol.,* vol. 64, No. 9, pp 4162–4168 (1990).

Oker–Blom, C., et al., "Rubella Virus Contains One Capsid Protein and Three Envelope Glycoproteins, E1, E2a, and E2b", *J. Virol.,* vol. 46, No. 3, pp 964–973 (1983).

Oker–Blom, C., "The Gene Order for Rubella Virus Structural Proteins is NH2–C–E2–E1–COOH", *J. Virol.,* vol. 51, No. 2, pp 354–358 (1984).

Ou, J.H., et al., "The 5'–terminal Sequences of the Genomic RNA's of Several Alphaviruses", *J. Mol. Biol.,* vol. 168; No. 1, pp 1–15 (1983).

Pugachev, K.V., et al., "Sindbis Vectors Suppress Secretion of Subviral Particles of Japanese Encephalitis Virus from Mammalian Cells Infected with SIN–JEV Recombinants", *Virology,* vol. 209, No. 1, pp 155–166 (1995).

Pugachev, K.V., et al., "Double–Subgenomic Sindbis Virus Recombinants Expressing Immunogenic Proteins of Japanese Encephalitis Virus Induce Significant Protection in Mice Against Letal JEV Infection", *Virology,* vol. 212, No. 2, pp 587–594 (1995).

Pugachev, K.V., et al. "Improvement of the Specific Infectivity of the Rubella Virus (RUB) Infectious Clone: Determinants of Cytopathogenicity Induced by RUB Map to the Nonstructural Proteins", *J. Virol.,* vol. 71, No. 1, pp 562–568 (1997).

Pugachev, K.V., et al., "Development of a Rubella Virus Vaccine Expression Vector: Use of a Picornavirus Internal Ribosome Entry Site Increases Stability of Expression", *J. Virol.,* vol. 74, No. 22, pp 10811–10815 (2000).

Pugachev, K.V., et al. "Infectious cDNA Clone of the RA27/3 Vaccine Strain of Rubella Virus", *Virology,* vol. 273, pp 189–197 (2000).

Rice, C.M., et al., "Production of Infectious RNA Transcripts from Sindbis Virus cDNA Clones: Mapping of Lethal Mutations, Rescue of a Temperature–Sensitive Marker", and In Vitro Mutagenesis to Generate Defined Mutants, *J. Virol.,* vol. 61, No. 12, pp 3809–3819 (1987).

Schlesinger, S., et al., "Alphavirus Vectors for Gene Expression and Vaccines", *Curr. Opin. Biotechnol.,* vol. 10, No. 5, pp 434–439 (1999).

Smerdou, C., et al., "Two–Helper RNA System for Production of Recombinant Semliki Forest Virus Particles", *J. Virol.,* vol. 73, No. 2, pp. 1092–1098 (1999).

Strauss, J.H., et al., "The Alphaviruses; Gene Expression, Replication, and Evolution", *Microbiol. Rev.,* vol. 58, No. 4, pp 491–562 (1994). (Abstract Only).

Takkinen, K., et al., "Nucleotide Sequence of the Rubella Virus Capsid Protein Gene Reveals an Unusually High G/C Content", *J. Gen. Virol.,* vol. 69, pp 603–612 (1988).

Vidgren, G., et al., "Nucleotide Sequence of the Genes Coding for the Membrane Glycoproteins E1 and E2 of Rubella Virus", *J. Gen. Virol.,* vol. 68, Pt. 9, pp 2347–2357 (1987).

Wang, C.Y., et al., "Construction of Rubella Virus Genome–Length cDNA Clones and Synthesis of Infectious RNA Transcripts", *J. Virol.,* vol. 68, No. 6, pp 3550–3557 (1994).

Waxham, M.N., et al., "Immunochemical Identification of Rubella Virus Hemagglutinin", *Virology,* vol. 126, No. 1, pp 194–203 (1983).

Waxham, M.N., et al., "Detailed Immunologic Analysis of the Structural Polypeptides of Rubella Virus Using Monoclonal Antibodies", *Virology,* vol. 143, No. 1, pp 153–165 (1985).

Weibel, R.E., et al., "Clinical and Laboratory Studies of Combined Live Measles, Mumps, and Rubella Vaccines Using the RA 27/3 Rubella Virus", *Proc. Soc. Exp. Biol. Med.,* vol. 165, No. 2, pp 323–326 (1980).

Zheng, D.X., et al., "Nucleotide sequence of the 24S Subgenomic Messenger RNA of a Vaccine Strain (HPV77) of Rubella Virus: Comparison With a Wild–Type Strain (M33)", *Gene,* vol. 82, No. 2, pp 343–349 (1989).

* cited by examiner

Robo 302/402 dsRobo 302

Robo 402/IRES siRobo 402

★ SG Promoter     ■ Foreign Gene

▨ IRES Element     ------ SG RNA

A.

B.

SEQUENCE LISTING

<160> NUMBER OF SEQ ID NOS: 17

<210> SEQ ID NO 1
<211> LENGTH: 9759
<212> TYPE: DNA
<213> ORGANISM: Artificial Sequence
<220> FEATURE:
<223> OTHER INFORMATION: Synthetic construct - Rubella

<400> SEQUENCE: 1

```
caatggaagc tatcggacct cgcttaggac tcccattccc atggagaaac tcctagatga     60
ggttcttgcc cccggtgggc cttataactt aaccgtcggc agttgggtaa gagaccacgt    120
ccgatcaatt gtcgagggcg cgtgggaagt gcgcgatgtt gttaccgctg cccaaaagcg    180
ggccatcgta gccgtgatac ccagacctgt gttcacgcag atgcaggtca gtgatcaccc    240
agcactccac gcaatttcgc ggtatacccg ccgccattgg atcgagtggg gccctaaaga    300
agccctacac gtcctcatcg acccaagccc gggcctgctc cgcgaggtcg ctcgcgttga    360
gcgccgctgg gtcgcactgt gcctccacag gacggcacgc aaactcgcca ccgccctggc    420
cgagacggcc agcgaggcgt ggcacgctga ctacgtgtgc gcgctgcgtg gcgcaccgag    480
cggccccttc tacgtccacc ctgaggacgt cccgcacggc ggtcgcgccg tggcggacag    540
atgcttgctc tactacacac ccatgcagat gtgcgagctg atgcgtacca ttgacgccac    600
cctgctcgtg gcggttgact tgtggccggt cgcccttgcg gcccacgtcg gcgacgactg    660
ggacgacctg ggcattgcct ggcatctcga ccatgacggc ggttgccccg ccgattgccg    720
cggagccggc gctgggccca cgcccggcta cacccgcccc tgcaccacac gcatctacca    780
agtcctgccg gacaccgccc accccgggcg cctctaccgg tgcgggcccc gcctgtggac    840
gcgcgattgc gccgtggccg aactctcatg ggaggttgcc caacactgcg ggcaccaggc    900
gcgcgtgcgc gccgtgcgat gcaccctccc tatccgccac gtgcgcagcc tccaacccag    960
cgcgcgggtc cgactcccgg acctcgtcca tctcgccgag gtgggccggt ggcggtggtt   1020
cagcctcccc cgccccgtgt tccagcgcat gctgtcctac tgcaagaccc tgagccccga   1080
cgcgtactac agcgagcgcg tgttcaagtt caagaacgcc ctgtgccaca gcatcacgct   1140
cgcgggcaat gtgctgcaag aggggtggaa gggcacgtgc gccgaggaag acgcgctgtg   1200
cgcatacgta gccttccgcg cgtggcagtc taacgccagg ttggcgggga ttatgaaagg   1260
cgcgaagcgc tgcgccgccg actctttgag cgtggccggc tggctggaca ccatttggga   1320
cgccattaag cggttcctcg gtagcgtgcc cctcgccgag cgcatggagg agtgggaaca   1380
ggacgccgcg gtcgccgcct tcgaccgcgg ccccctcgag gacggcgggc gccacttgga   1440
caccgtgcaa cccccaaaat cgccgccccg ccctgagatc gccgcgacct ggatcgtcca   1500
cgcagccagc gaagaccgcc attgcgcgtg cgctccccgc tgcgacgtcc cgcgcgaacg   1560
tccttccgcg cccgccggcc agccggatga cgaggcgctc atcccgccgt ggctgttcgc   1620
cgagcgccgt gccctccgct gccgcgagtg ggatttcgag gctctccgcg cgcgcgccga   1680
tacggcggcc gcgcccgccc cgccggctcc acgccccgcg cggtacccca ccgtgctcta   1740
ccgccacccc gcccaccacg gcccgtggct caccccttgac gagccgggcg aggctgacgc  1800
ggccctggtc ttatgcgacc cacttggcca gccgctccgg ggccctgaac gccacttcgc   1860
cgccggcgcg catatgtgcg cgcaggcgcg ggggctccag gcttttgtcc gtgtcgtgcc   1920
tccacccgag cgcccctggg ccgacggggg cgccagagcg tgggcgaagt tcttccgcgg   1980
```

-continued

```
ctgcgcctgg gcgcagcgct tgctcggcga gccagcagtt atgcacctcc catacaccga    2040
tggcgacgtg ccacagctga tcgcactggc tttgcgcacg ctggcccaac agggggccgc    2100
cttggcactc tcggtgcgtg acctgcccgg gggtgcagcg ttcgacgcaa acgcggtcac    2160
cgccgccgtg cgcgctggcc cccgccagtc cgcggccgcg tcaccgccac ccggcgaccc    2220
cccgccgccg cgccgcgcac ggcgatcgca acggcactcg gacgctcgcg gcactccgcc    2280
ccccgcgcct gcgcgcgacc cgccgccgcc cgccccagc ccgcccgcgc caccccgcgc     2340
tggtgacccg gtccctccca ttcccgcggg gccggcggat cgcgcgcgtg acgccgagct    2400
ggaggtcgcc tgcgagccga gcggcccccc cacgtcaacc agggcagacc cagacagcga    2460
catcgttgaa agttacgccc gcgccgccgg acccgtgcac ctccgagtcc gcgacatcat    2520
ggacccaccg cccggctgca aggtcgtggt caacgccgcc aacgaggggc tactggccgg    2580
ctctggcgtg tgcggtgcca tctttgccaa cgccacggcg gccctcgctg caaactgccg    2640
gcgcctcgcc ccatgcccca ccggcgaggc agtggcgaca cccggccacg gctgcgggta    2700
cacccacatc atccacgccg tcgcgccgcg gcgtcctcgg gaccccgccg ccctcgagga    2760
gggcgaagcg ctgctcgagc gcgcctaccg cagcatcgtc gcgctagccg ccgcgcgtcg    2820
gtgggcgtgt gtcgcgtgcc ccctcctcgg cgctggcgtc tacggctggt ctgctgcgga    2880
gtccctccga gccgcgctcg cggctacgcg caccgagccc gtcgagcgcg tgagcctgca    2940
catctgccac cccgaccgcg ccacgctgac gcacgcctcc gtgctcgtcg gcgcggggct    3000
cgctgccagg cgcgtcagtc ctcctccgac cgagcccctc gcatcttgcc ccgccggtga    3060
cccgggccga ccggctcagc gcagcgcgtc gcccccagcg accccccttg gggatgccac    3120
cgcgcccgag ccccgcggat gccagggtg cgaactctgc cggtacacgc gcgtcaccaa     3180
tgaccgcgcc tatgtcaacc tgtggctcga gcgcgaccgc ggcgccacca gctgggccat    3240
gcgcattccc gaggtggttg tctacgggcc ggagcacctc gccacgcatt ttccattaaa    3300
ccactacagt gtgctcaagc ccgcggaggt caggcccccg cgaggcatgt gcgggagtga    3360
catgtggcgc tgccgcggct ggcatggcat gccgcaggtg cggtgcaccc cctccaacgc    3420
tcacgccgcc ctgtgccgca caggcgtgcc ccctcgggcg agcacgcgag cggcgagct     3480
agacccaaac acctgctggc tccgcgccgc cgccaacgtt gcgcaggctg cgcgcgcctg    3540
cggcgcctac acgagtgccg ggtgccccaa gtgcgcctac ggccgcgccc tgagcgaagc    3600
ccgcactcat gaggacttcg ccgcgctgag ccagcggtgg agcgcgagcc acgccgatgc    3660
ctcccctgac ggcaccggag atcccctcga cccctgatg gagaccgtgg gatgcgcctg     3720
ttcgcgcgtg tgggtcggct ccgagcatga ggccccgccc gaccacctcc tggtgtccct    3780
tcaccgtgcc ccaaatggtc cgtggggcgt agtgctcgag gtgcgtgcgc gccccgaggg    3840
gggcaacccc accggccact tcgtctgcgc ggtcggcggc ggcccacgcc gcgtctcgga    3900
ccgcccccac ctctggcttg cggtcccccct gtctcggggc ggtggcacct gtgccgcgac    3960
cgacgagggg ctggcccagg cgtactacga cgacctcgag gtgcgccgcc tcggggatga    4020
cgccatggcc cgggcggccc tcgcatcagt ccaacgccct cgcaaaggcc cttacaatat    4080
cagggtatgg aacatggccg caggcgctgg caagactacc cgcatcctcg ctgccttcac    4140
gcgcgaagac ctttacgtct gccccaccaa tgcgctcctg cacgagatcc aggccaaact    4200
ccgcgcgcgc gatatcgaca tcaagaacgc cgccacctac gagcgccggc tgacgaaacc    4260
gctcgccgcc taccgccgca tctacatcga tgaggcgttc actctcggcg gcgagtactg    4320
```

```
cgcgttcgtt gccagccaaa ccaccgcgga ggtgatctgc gtcggtgatc gggaccagtg  4380
cggcccacac tacgccaata actgccgcac ccccgtccct gaccgctggc ctaccgagcg  4440
ctcgcgccac acttggcgct tccccgactg ctgggcggcc cgcctgcgcg cggggctcga  4500
ttatgacatc gagggcgagc gcaccggcac cttcgcctgc aacctttggg acggccgcca  4560
ggtcgacctt cacctcgcct tctcgcgcga aaccgtgcgc cgccttcacg aggctggcat  4620
acgcgcatac accgtgcgcg aggcccaggg tatgagcgtc ggcaccgcct gcatccatgt  4680
aggcagagac ggcacggacg ttgccctggc gctgacacgc gacctcgcca tcgtcagcct  4740
gacccgggcc tccgacgcac tctacctcca cgagctcgag gacggctcac tgcgcgctgc  4800
ggggctcagc gcgttcctcg acgccggggc actggcggag ctcaaggagg ttcccgctgg  4860
cattgaccgc gttgtcgccg tcgagcaggc accaccaccg ttgccgcccg ccgacggcat  4920
ccccgaggcc caagacgtgc cgcccttctg ccccgcact  ctggaggagc tcgtcttcgg  4980
ccgtgccggc caccccatt acgcggacct caaccgcgtg actgagggcg aacgagaagt  5040
gcggtacatg cgcatctcgc gtcacctgct caacaagaat cacaccgaga tgcccggaac  5100
ggaacgcgtt ctcagtgccg tttcgccgtg cggctaccgc gcgggcgagg atgggtcgac  5160
cctccgcact gctgtggccc gccagcaccc gcgccctttt cgccagatcc caccccgcg  5220
cgtcactgct ggggtcgccc aggagtggcg catgacgtac ttgcgggaac ggatcgacct  5280
cactgatgtc tacacgcaga tgggcgtggc cgcgcgggag ctcaccgacc gctacgcgcg  5340
ccgctatcct gagatcttcg ccggcatgtg taccgcccag agcctgagcg tccccgcctt  5400
cctcaaagcc accttgaagt gcgtagacgc cgccctcggc cccagggaca ccgaggactg  5460
ccacgccgct caggggaaag ccggccttga gatccgggcg tgggccaagg agtgggttca  5520
ggttatgtcc ccgcatttcc gcgcgatcca aagatcatc atgcgcgcct tgcgcccgca  5580
attccttgtg gccgctggcc atacggagcc gaggtcgat gcgtggtggc aggcccatta  5640
caccaccaac gccatcgagg tcgacttcac tgagttcgac atgaaccaga ccctcgctac  5700
tcgggacgtc gagctcgaga ttagcgccgc tctcttgggc ctcccttgcg ccgaagacta  5760
ccgcgcgctc cgcgccggca gctactgcac cctgcgcgaa ctgggctcca ctgagaccgg  5820
ctgcgagcgc acaagcggcg agcccgccac gctgctgcac aacaccaccg tggccatgtg  5880
catggccatg cgcatggtcc ccaaaggcgt gcgctgggcc gggattttcc agggtgacga  5940
tatggtcatc ttcctccccg agggcgcgcg cagcgcggca ctcaagtgga ccccgccga  6000
ggtgggcttg tttggcttcc acatcccggt gaagcacgtg agcaccccta ccccagctt   6060
ctgcgggcac gtcggcaccg cggcggcct cttccatgat gtcatgcacc aggcgatcaa  6120
ggtgctttgc cgccgtttcg acccagacgt gcttgaagaa cagcaggtgg ccctcctcga  6180
ccgcctccgg ggggtctacg cggctctgcc tgacaccgtt gccgccaatg ctgcgtacta  6240
cgactacagc gcggagcgcg tcctcgctat cgtgcgcgaa cttaccgcgt acgcgcgggg  6300
gcgcggcctc gaccacccgg ccaccatcgg cgcgctcgag gagattcaga ccccctacgc  6360
gcgcgccaat ctccacgacg ccgactaacg ccctgtacg tggggccttt aatcttacct   6420
actctaacca ggtcatcacc caccgttgtt cgccgcatc tggtgggtac ccaacttttg   6480
ccattcggga gagccccagg gtgcccgaat ggcttctact accccatca ccatggagga   6540
cctccagaag gccctcgagg cacaatcccg cgccctgcgc gcggaactcg ccgccggcgc  6600
ctcgcagtcg cgccggccgc ggccgccgcg acagcgcgac tccagcacct ccggagatga  6660
ctccggccgt gactccggag ggccccgccg ccgccgcggc aaccggggcc gtggccagcg  6720
```

-continued

```
cagggactgg tccagggccc cgcccccccc ggaggagcgg caagaaactc gctcccagac   6780
tccggccccg aagccatcgc gggcgccgcc acaacagcct caaccccgc gcatgcaaac    6840 cgggcgtggg ggctctgccc cgcgcccga gctgggccca ccgaccaacc cgttccaagc    6900
agccgtggcg cgtggcctgc gcccgcctct ccacgaccct gacaccgagg cacccaccga   6960
ggcctgcgtg acctcgtggc tttggagcga gggcgaaggc gcggtctttt accgcgtcga   7020
cctgcatttc accaacctgg gcaccccccc actcgacgag gacggccgct gggaccctgc   7080
gctcatgtac aacccttgcg ggcccgagcc gcccgctcac gtcgtccgcg cgtacaatca   7140
acctgccggc gacgtcaggg gcgtttgggg taaaggcgag cgcacctacg ccgagcagga   7200
cttccgcgtc ggcggcacgc gctggcaccg actgctgcgc atgccagtgc gcggcctcga   7260
cggcgacagc gccccgcttc cccccacac caccgagcgc attgagaccc gctcggcgcg    7320
ccatccttgg cgcatccgct tcggtgcccc ccaggccttc cttgccgggc tcttgctcgc   7380
cacggtcgcc gttggcaccg cgcgcgccgg gctccagccc cgcgctgata tggcggcacc   7440
tcctacgctg ccgcagcccc cctgtgcgca cgggcagcat tacggccacc accaccatca   7500
gctgccgttc ctcgggcacg acggccatca tggcggcacc ttgcgcgtcg ccagcatta    7560 ccgaaacgcc agcgacgtgc tgcccggcca ctggctccaa ggcggctggg gttgctacaa   7620
cctgagcgac tggcaccagg gcactcatgt ctgtcatacc aagcacatgg acttctggtg   7680
tgtggagcac gaccgaccgc cgcccgcgac cccgacgcct ctcaccaccg cggcgaactc   7740
cacgaccgcc gccaccccg ccactgcgcc ggccccctgc cacgccggcc tcaatgacag    7800
ctgcggcggc ttcttgtctg ggtgcgggcc gatgcgcctg cgccacggcg ctgacacccg   7860
gtgcggtcgc ttgatctgcg ggctgtccac caccgcccag tacccgccta cccggtttgg   7920
ctgcgctatg cggtggggcc ttcccccctg ggaactggtc gtccttaccg cccgccccga   7980
agacggctgg acttgccgcg gcgtgcccgc ccatccaggc gcccgctgcc ccgaactggt   8040
gagccccatg ggacgcgcga cttgctcccc agcctcggcc ctctggctcg ccacagcgaa   8100
cgcgctgtct cttgatcacg ccctcgcggc cttcgtcctg ctggtcccgt gggtcctgat   8160
atttatggtg tgccgccgcg cctgtcgccg ccgcggcgcc gccgccgccc tcaccgcggt   8220
cgtcctgcag gggtacaacc cccccgccta tggcgaggag gctttcacct acctctgcac   8280
tgcaccgggg tgcgccactc aagcacctgt ccccgtgcgc ctcgctggcg tccgttttga   8340
gtccaagatt gtggacggcg gctgctttgc cccatgggac ctcgaggcca ctggagcctg   8400
catttgcgag atccccactg atgtctcgtg cgagggcttg ggggcctggg tacccgcagc   8460
cccttgcgcg cgcatctgga atggcacaca gcgcgcgtgc accttctggg ctgtcaacgc   8520
ctactcctct ggcgggtacg cgcagctggc ctcttacttc aaccctggcg gcagctacta   8580
caagcagtac caccctaccg cgtgcgaggt tgaacctgcc ttcggacaca gcgacgcggc   8640
ctgctggggc ttccccaccg acaccgtgat gagcgtgttc gcccttgcta gctacgtcca   8700
gcaccctcac aagaccgtcc gggtcaagtt ccatacagag accaggaccg tctggcaact   8760
ctccgttgcc ggcgtgtcgt gcaacgtcac cactgaacac ccgttctgca acacgccgca   8820
cggacaactc gaggtccagg tcccgccga ccccggggac ctggttgagt acattatgaa    8880
ttacaccggc aatcagcagt cccggtgggg cctcgggagc ccgaattgcc acggcccga    8940 ttgggcctcc ccggtttgcc aacgccattc ccctgactgc tcgcggcttg tgggggccac   9000
gccagagcgc cccggctgc gcctggtcga cgccgacgac cccctgctgc gcactgcccc   9060
```

| | |
|---|---:|
| tggacccggc gaggtgtggg tcacgcctgt cataggctct caggcgcgca agtgcggact | 9120 |
| ccacatacgc gctggaccgt acggccatgc taccgtcgaa atgcccgagt ggatccacgc | 9180 |
| ccacaccacc agcgacccct ggcatccacc gggcccttg gggctgaagt tcaagacagt | 9240 |
| tcgcccggtg gccctgccac gcacgttagc gccaccccgc aatgtgcgtg tgaccgggtg | 9300 |
| ctaccagtgc ggtaccccg cgctggtgga aggccttgcc cccggggag gcaattgcca | 9360 |
| tctcaccgtc aatggcgagg acctcggcgc cgtccccct gggaagttcg tcaccgccgc | 9420 |
| cctcctcaac accccccgc cctaccaagt cagctgcggg ggcgagagcg atcgcgcgac | 9480 |
| cgcgcgggtc atcgacccg ccgcgcaatc gtttaccggc gtggtgtatg cacacacac | 9540 |
| cactgctgtg tcggagaccc ggcagacctg ggcggagtgg gctgctgccc attggtggca | 9600 |
| gctcactctg ggcgccattt cgccctccc actcgctggc ttactcgctt gctgtgccaa | 9660 |
| atgcttgtac tacttgcgcg cgctatagc gcctcgctag tgggcccccg cgcgaaaccc | 9720 |
| gcactaggcc actagatccc cgcacctgtt gctgtatag | 9759 |

<210> SEQ ID NO 2
<211> LENGTH: 1727
<212> TYPE: DNA
<213> ORGANISM: Rubella virus

<400> SEQUENCE: 2

| | |
|---|---:|
| caatggaagc tatcggacct cgcttaggac tcccattccc atggagaagc tcctagatga | 60 |
| ggttcttgcc cccggtgggc cttataactt aaccgtcggc agttgggtaa gagaccacgt | 120 |
| ccgatcaatt gtcgagggcg cgtgggaagt gcgcgatgtt gttaccgctg cccaaaagcg | 180 |
| ggccatcgta ccgtgatac ccagacctgt gttcacgcag atgcaggtca gtgatcaccc | 240 |
| agcactccac gcaatttcgc ggtatacccg ccgccattgg atcgagtggg gccctaaaga | 300 |
| agccctacac gtcctcatcg acccaagccc gggcctgctc cgcgaggtcg ctcgcgttga | 360 |
| gcgccgctgg gtcgcactgt gcctccacag gacggcacgc aaactcgcca ccgccctggc | 420 |
| cgagacggcc ggcgaggcgt ggcacgctga ctacgtgtgc gcgctgcgtg gcgcaccgag | 480 |
| cggcccttc tacgtccacc ctgaggacgt cccgcacggc ggtcgcgccg tggcggacag | 540 |
| atgcttgctc tactacacac ccatgcagat gtgcagctg atgcgtacca ttgacgccac | 600 |
| cctgctcgtg gcggttgact tgtggccggt cgccttgcg gccacgtcg gcgacgactg | 660 |
| ggacgacctg gcattgcct ggcatctcga ccatgacggc ggttgccccg ccgattgccg | 720 |
| cggagccggc gctgggccca cgcccggcta cacccgcccc tgcaccacac gcatttacca | 780 |
| agtcctgccg gacaccgccc accccgggcg cctctaccgg tgcggccccc gcctgtggac | 840 |
| gcgcgattgc gccgtggccg aactctcatg ggaggttgcc caacactgcg gcaccaggc | 900 |
| gcgcgtgcgc gccgtgcgat gcaccctccc tatccgccac gtgcgcagcc tccaacccag | 960 |
| cgcgcgggtc cgactcccgg acctcgtcca tctcgccgag gtgggccggt ggcggtggtt | 1020 |
| cagcctcccc cgccccgtgt tccagcgcat gctgtcctac tgcaagaccc tgagccccga | 1080 |
| cgcgtactac agcgagcgcg tgttcaagtt caagaacgcc ctgagccaca gcatcacgct | 1140 |
| cgcgggcaat gtgctgcaag agggtggaa gggcacgtgc gccgaggaag acgcgctgtg | 1200 |
| cgcatacgta gccttccgcg cgtggcagtc taacgccagg ttggcgggga ttatgaaagg | 1260 |
| cgcgaagcgc tgcgccgccg actctttgag cgtggccggc tggctggaca ccatttggga | 1320 |
| cgccattaag cggttcttcg gtagcgtgcc cctcgccgag cgcatggagg agtgggaaca | 1380 |
| ggacgccgcg gtcgccgcct tcgaccgcgg ccccctcgag gacggcgggc gccacttgga | 1440 |

-continued

```
caccgtgcaa ccccccaaaat cgccgccccg ccctgagatc gccgcgacct ggatcgtcca      1500
cgcagccagc gcagaccgcc attgcgcgtg cgctccccgc tgcgacgtcc cgcgcgaacg      1560
tccttccgcg cccgccggcc cgccggatga cgaggcgctc atcccgccgt ggctgttcgc      1620
cgagcgccgt gccctccgct gccgcgagtg ggatttcgag gctctccgcg cgcgcgccga      1680
tacggcggcc gcgtccgccc cgctggctcc ccgccccgcg cggtacc                   1727
```

<210> SEQ ID NO 3
<211> LENGTH: 2558
<212> TYPE: DNA
<213> ORGANISM: Rubella virus

<400> SEQUENCE: 3

```
gctagccgcc gcgcgtcggt gggcgtgtgt cgcgtgcccc ctcctcggcg ctggcgtcta        60
cggctggtct gctgcggagt ccctccgagc gcgctcgcg gctacgcgca ccgagcccgt       120
cgagcgcgtg agcctgcaca tctgccaccc cgaccgcgcc acgctgacgc acgcctccgt       180
gctcgtcggc gcggggctcg ctgccaggcg cgtcagtcct cctccgaccg agcccctcgc       240
atcttgcccc gccggtgacc cgggccgacc ggctcagcgc agcgcgtcgc ccccagcgac       300 ccccccttggg gatgccaccg cgcccgagcc ccgcggatgc cagggggtgcg aactctgccg       360 gtgcacgcgc gtcaccaatg accgcgccta tgtcaacctg tggctcgagc gcgaccgcgg       420
cgccaccagc tgggccatgc gcattcccga ggtggttgtc tacgggccgg agcacctcgc       480
cacgcatttt ccattaaacc actacagtgt gctcaagccc gcggaggtca ggcccccgcg       540
aggcatgtgc gggagtgaca tgtggcgctg ccgcggctgg catggcatgc cgcaggtgcg       600 gtgcacccccc tccaacgctc acgccgccct gtgccgcaca ggcgtgcccc ctcgggcgag       660
cacgcgaggc ggcgagctag acccaaacac ctgctggctc cgcgccgccg ccaacgttgc       720
gcaggctgcg cgcgcctgcg gcgcctacac gagtgccggg tgccccaagt gcgcctacgg       780
ccgcgccctg agcgaagccc gcactcatga ggacttcgcc gcgctgagcc agcggtggag       840
cgcgagccac gccgatgcct cccctgacgg caccggagat cccctcgacc ccctgatgga       900
gaccgtggga tgcacctgtt cgcgcgtgtg ggtcggctcc gagcatgagg ccccgcccga       960
ccaactcctg tgtccccttc accgtgcccc aaatggtccg tggggcgtag tgctcgaggt      1020
gcgtgcgcgc cccgaggggg gcaaccccac cggccacttc gtctgcgcgg tcggcggcgg      1080
cccacgccgc gtctcggacc gccccaccct ctggcttgcg gtccccctgt ctcggggcgg      1140
tggcacctgt gccgcgaccg acgagggggct ggcccaggcg tactacgacg acctcgaggt      1200
gcgccgcctc ggggatgacg ccatggcccg ggcggccctc gcatcagtcc aacgccctcg      1260 caaaggcccct tacaatatca gggtatggaa catggccgca ggcgctggca agactacccg      1320
catcctcgct gccttcacgc gcgaagacct ttacgtctgc cccaccaatg cgctcctgca      1380
cgagatccag gccaaactcc gcgcgcgcga tatcgacttc aagaacgccg ccacctacga      1440
gcgccggctg acgaaaccgc tcgccgccta ccgccgcatc tacatcgatg aggcgttcac      1500
tctcggcggc gagtactgcg cgttcgttgc cagccaaacc accgcggagg tgatctgcgt      1560
cggtgatcgg gaccagtgcg gcccacacta cgccaataac tgccgcaccc ccgtccctga      1620
ccgctggcct accgagagct cacgccacac ttggcgcttc cccgactgct gggcggcccg      1680
cctgcgcgcg ggctcgatt atgacatcga gggcgagcgc accggcacct tcgcctgcaa      1740
cctttgggac ggccgccagg tcgaccttca cctcgccttc tcgcgcgaaa ccgtgcgccg      1800
```

```
ccttcacgag gctggcatac gcgcatacac cgtgcgcgag gcccagggta tgagcgtcgg      1860
caccgcctgc atccatgtag gcagagacgg cacggacgtt gccctggcgc tgacacgcga      1920
cctcgccatc gtcagcctga cccgggcctc cgacgcactc tacctccacg agctcgagga      1980
cggctcactg cgcgctgcgg ggctcagcgc gttcctcgac gccggggcac tggcggagct      2040
caaggaggtt cccgctggca ttgaccgcgt tgtcgccgtc gagcaggcac caccaccgtt      2100
gccgcccgcc gacggcatcc ccgaggccca agacgtgccg cccttctgcc cccgcactct      2160
ggaggagctc gtcttcggcc gtgccggcca cccccattac gcggacctca accgcgtgac      2220
tgagggcgaa cgagaagtgc ggtacatgcg catctcgcgt cacctgctca acaagaatca      2280
caccgagatg cccggaacgg aacgcgttct cagtgccgtt tgcgccgtgc ggcgctaccg      2340
cgcgggcgag gatgggtcga ccctccgcac tgctgtggcc cgccagcacc cgcgcccttt      2400
tcgccagatc ccaccccgc gcgtcactgc tggggtcgcc caggagtggc gcatgacgta       2460
cttgcgggaa cggatcgacc tcactgatgt ctacacgcag atgggcgtgg ccgcgcggga      2520
gctcaccgac cgctacgcgc gccgctatcc tgagatct                              2558

<210> SEQ ID NO 4
<211> LENGTH: 29
<212> TYPE: DNA
<213> ORGANISM: Artificial Sequence
<220> FEATURE:
<223> OTHER INFORMATION: Synthetic primer

<400> SEQUENCE: 4
gggaagcttg cacgacacgg acaaaagcc                                          29

<210> SEQ ID NO 5
<211> LENGTH: 17
<212> TYPE: DNA
<213> ORGANISM: Artificial Sequence
<220> FEATURE:
<223> OTHER INFORMATION: Synthetic primer

<400> SEQUENCE: 5
tagtcttcgg cgcaagg                                                       17

<210> SEQ ID NO 6
<211> LENGTH: 47
<212> TYPE: DNA
<213> ORGANISM: Artificial Sequence
<220> FEATURE:
<223> OTHER INFORMATION: Synthetic primer

<400> SEQUENCE: 6
cgcgaattct tttttttttt tttttttttc tatacagcaa caggtgc                      47

<210> SEQ ID NO 7
<211> LENGTH: 55
<212> TYPE: DNA
<213> ORGANISM: Artificial Sequence
<220> FEATURE:
<223> OTHER INFORMATION: Synthetic primer

<400> SEQUENCE: 7
tcgaagctta tttaggtgac actatagcaa tggaagctat cggacctcgc ttagg             55

<210> SEQ ID NO 8
<211> LENGTH: 17
<212> TYPE: DNA
<213> ORGANISM: Artificial Sequence
```

```
<220> FEATURE:
<223> OTHER INFORMATION: Synthetic primer

<400> SEQUENCE: 8
tttgccaacg ccacggc                                                    17

<210> SEQ ID NO 9
<211> LENGTH: 17
<212> TYPE: DNA
<213> ORGANISM: Artificial Sequence
<220> FEATURE:
<223> OTHER INFORMATION: Synthetic primer

<400> SEQUENCE: 9
agctcaccga ccgctac                                                    17

<210> SEQ ID NO 10
<211> LENGTH: 17
<212> TYPE: DNA
<213> ORGANISM: Artificial Sequence
<220> FEATURE:
<223> OTHER INFORMATION: Synthetic primer

<400> SEQUENCE: 10
agctcaccga ccgctac                                                    17

<210> SEQ ID NO 11
<211> LENGTH: 29
<212> TYPE: DNA
<213> ORGANISM: Artificial Sequence
<220> FEATURE:
<223> OTHER INFORMATION: Synthetic primer

<400> SEQUENCE: 11
gcctctagat tcgggcaccc tggggctct                                       29

<210> SEQ ID NO 12
<211> LENGTH: 55
<212> TYPE: DNA
<213> ORGANISM: Artificial Sequence
<220> FEATURE:
<223> OTHER INFORMATION: Synthetic primer

<400> SEQUENCE: 12
gaatctagag gccttcgaac gcgttaacat gcatgtcctc gctatcgtgc gcgaa          55

<210> SEQ ID NO 13
<211> LENGTH: 18
<212> TYPE: DNA
<213> ORGANISM: Artificial Sequence
<220> FEATURE:
<223> OTHER INFORMATION: Synthetic primer

<400> SEQUENCE: 13
gaagcggatg cgccaagg                                                   18

<210> SEQ ID NO 14
<211> LENGTH: 29
<212> TYPE: DNA
<213> ORGANISM: Artificial Sequence
<220> FEATURE:
<223> OTHER INFORMATION: Synthetic primer

<400> SEQUENCE: 14
cacaatgcat aattccgccc ctctccctc                                       29
```

```
<210> SEQ ID NO 15
<211> LENGTH: 21
<212> TYPE: DNA
<213> ORGANISM: Artificial Sequence
<220> FEATURE:
<223> OTHER INFORMATION: Synthetic primer

<400> SEQUENCE: 15
catggttgtg gcaagcttat c                                      21

<210> SEQ ID NO 16
<211> LENGTH: 28
<212> TYPE: DNA
<213> ORGANISM: Artificial Sequence
<220> FEATURE:
<223> OTHER INFORMATION: Synthetic primer

<400> SEQUENCE: 16
cgctagcgct tctactaccc ccatcacc                               28

<210> SEQ ID NO 17
<211> LENGTH: 18
<212> TYPE: DNA
<213> ORGANISM: Artificial Sequence
<220> FEATURE:
<223> OTHER INFORMATION: Synthetic primer

<400> SEQUENCE: 17
gaagcggatg cgccaagg                                          18
```

HIGHLY INFECTIOUS RUBELLA VIRUS DNA CONSTRUCTS AND METHODS OF PRODUCTION

CROSS-REFERENCE TO RELATED APPLICATIONS

This is a continuation-in-part of U.S. patent application Ser. No. 09/557,232, filed Apr. 24, 2000, now abandoned which is a continuation of U.S. patent application Ser. No. 08/999,733 filed Sep. 2, 1997, now U.S. Pat. No. 6,054,573, which is a continuation-in-part of U.S. patent application Ser. No. 08/459,041 filed Jun. 2, 1995, now U.S. Pat. No. 5,663,065, which is a continuation-in-part of U.S. patent application Ser. No. 08/093,453, filed Jul. 19, 1993, now U.S. Pat. No. 5,439,814, which is a continuation of U.S. patent application Ser. No. 07/722,334, filed on Jun. 28, 1991, now abandoned. This application claims the benefit of U.S. Provisional Patent Application Ser. No. 60/329,686, filed Oct. 15, 2001.

The U.S. Government has rights in this invention arising out of National Institutes of Health (NIAID) grant number AI-21389.

FIELD OF THE INVENTION

The present invention relates to the field of molecular virology and, more particularly, to construction of highly infectious rubella virus cDNA clones and to expression constructs based on rubella virus infectious clones.

BACKGROUND OF THE INVENTION

Rubella virus is a major human pathogen. Infection with rubella virus can cause serious birth defects and chronic disease. There was a mini-epidemic of both rubella and congenital rubella syndrome in the United States between 1989 and 1991.

Rubella was first described in the eighteenth century in Germany. The symptoms of a rash and mild fever were similar to those of measles, so the disease was given the name German measles. The name "rubella" was coined in 1814 when physicians realized that the disease was unique and was not merely a variant of scarlatina (scarlet fever) or rubeola (measles).

Rubella is a relatively harmless disease in young children. However, during the first trimester of pregnancy, rubella virus infection can cause fetal death. If the fetus survives, it may be born deaf or have cataracts, cardiac abnormalities, microcephaly, motor deficits or other congenital anomalies. The infant may also be born with thrombocytopenic purpura, hepatosplenomegaly, icterus, anemia, and low birth weight. The presence of one or more of these defects has been termed "congenital rubella syndrome" or CRS.

The rubella virus was isolated in 1962 at the beginning of a worldwide rubella epidemic which lasted from 1962 to 1965. This epidemic peaked in the United States in 1964, resulting in the birth of approximately 20,000 infants exhibiting CRS.

Scientists began development of an effective vaccine against the rubella virus during the rubella epidemic. Effective attenuated vaccines became available in the late 1960's and are still used today. These attenuated vaccines are live viruses that have been passaged to reduce their virulence. Attenuated vaccines produce immunity, but can cause disease. Protection is believed to persist for at least 15 years after inoculation with the attenuated rubella vaccine.

Various vaccination schedules have been set up in different parts of the world to eliminate rubella infection, especially of the human fetus. The rubella immunization program established in Great Britain requires vaccination of all girls between the ages of 10 and 14. The United States immunization program vaccinates infants at approximately 15 months and requires a certificate of vaccination prior to attending school. The United States program is designed to eradicate the disease among the population that is most responsible for transmission of rubella, whereas the program of Great Britain seeks to achieve complete protection for those at risk for pregnancy. One disadvantage to the United States program is that protection against rubella may dissipate at the very time when immunity is most needed, namely, during the child-bearing years.

Vaccination of women of child-bearing age having undetectable antibody titers is recommended in both the United States and Great Britain. However, there are several risks to this procedure. First, there is a risk that these women may be pregnant and not be aware of their pregnancy, or they may become pregnant within a few months following immunization. Vaccination against rubella is contraindicated in pregnant women because the live virus in the vaccine can cross the placenta and infect the fetus. Pregnant women who have not previously been infected with the rubella virus or who have not been vaccinated prior to becoming pregnant are advised to refrain from becoming vaccinated during their pregnancy. These women are therefore at risk for contracting rubella by coming in contact with infectious persons, including those recently vaccinated with the attenuated vaccine.

Vaccination of older women has been associated with chronic arthritis and neurological symptoms. Scientists believe that these symptoms may be due to the persistent nature of the attenuated rubella virus in the currently available vaccines.

Rubella virus is a small, quasi-spherical, enveloped, nonsegmented, plus-strand RNA virus that is the the sole member of the rubivirus genus of the togavirus family (Togaviridae). Molecular biology of rubella virus is summarized by Frey, T. K. in *Adv. Virus Res.* 44:69–160 (1994). One other member of the togavirus family is alphaviruses (see Strauss, J. H., and E. G. Strauss, *Microbiol. Rev.* 58:491–562. (1994) for a detailed description), which include a number of viruses pathogenic for vertebrates, including humans. The rubella virion (virus particle) consists of single-stranded RNA encapsidated in an icosahedral nucleocapsid surrounded by a lipid envelope. Multiple copies of a viral protein, designated the C protein (MW (molecular weight)=32,000–38,000 daltons), make up the nucleocapsid. Two types of viral glycoprotein, designated E1 and E2 (MW=53,000–58,000 daltons and 42,000–48,000 daltons, respectively), are embedded in the envelope, as reported by Waxham, M. N. and Wolinsky, J. S., *Virology* 126:194–203 (1983). The E2 glycoprotein has been further subdivided into two subgroups, designated E2a and E2b, by their ability to migrate differently when resolved by polyacrylamide gel electrophoresis, as described by Oker-Blom, C., et al., *J. Virol.* 46:964–973 (1983). E1 is the viral hemagglutinin. Neutralizing epitopes have been found on both E1 and E2 by Waxham, M. N. and Wolinsky, J. S., *Virology* 143:153–165 (1985) and Green, K. Y., and Dorsett, P. H., *J. Virol.*, 57:893–898 (1986).

The rubella genome consists of RNA of positive polarity that is roughly 10,000 nucleotides long and is capped and polyadenylated. In infected cells, three viral RNA species are synthesized: the genomic RNA, which also is the mRNA for translation of the nonstructural proteins (whose function is in viral RNA synthesis) from a long open reading frame (ORF) at the 5' end of the genome; a complementary genome-length RNA of minus polarity which is the template for synthesis of plus-strand RNA species; and a subgenomic (SG) RNA which is initiated internally and contains the sequences of the 3'-terminal one-third of the genome (3327 nucleotides) and serves as the mRNA for the translation of the structural proteins. The structural proteins are proteolytically processed from a polyprotein precursor during translation. The order of these proteins in the polyprotein is NH$_2$—C-E2-E1—COOH, as reported by Oker-Blom, C., et al. (1983); Oker-Blom, C., *J. Virol.* 51:354–358 (1984). In the other togavirus genus, the alphaviruses, synthesis of the SG RNA is directed by a short, approximately 25 nucleotide sequence located immediately upstream from the SG start site known as the SG promoter, as reported by Strauss, et al., *Microbiol. Rev.* 58:491–562 (1994). The exact location of the SG promoter in rubella virus genome is not known.

Recombinant vaccines are based on live microorganisms which have been genetically manipulated so that they are not pathogenic, but result in immunity against the virulent organism. Recombinant vaccines can only cause disease if a rare genetic mutation or recombinant event occurs which allows the microorganism to revert to wild type. A recombinant vaccine is generally safer and more effective than an attenuated vaccine because the engineered mutations remove or inactivate only specific portions of the genome, whereas attenuated vaccines contain random mutations. In order to develop a recombinant vaccine, one must first have the nucleic acid sequence of the entire viral genome, including both the information required for infection and at least limited replication of the virus, and for antigenicity. Once the entire sequence has been determined, a cDNA clone can be produced that is infectious and can be modified to be non-virulent.

An infectious cDNA clone is a complete DNA copy of an RNA virus genome contained in a vector, such as a plasmid, from which RNA transcripts of the genome can be synthesized in vitro. In the case of positive-polarity RNA viruses such as rubella, such transcripts are infectious when transfected into cells. The development of an infectious clone is a landmark event in the molecular biology of any RNA virus. Although an infectious clone for rubella virus has been described (Wang, et al., *J. Virol.* 68:3550–3557 (1994)), this cDNA clone displayed low infectivity (approximately 5 plaques/10 µg of transcripts). Increasing the infectivity of this clone would increase the efficiency of a recombinant attenuated rubella vaccine derived from the clone and would provide an improved molecular biology tool for studying rubella virus replication.

However, successful generation of highly infectious cDNA clones has often been problematic due to the presence of mutations in the virus RNA template population caused by the inherent mutability of RNA viruses, the relatively low fidelity of the DNA polymerases used in cDNA synthesis, instability and toxicity of viral sequences in bacterial hosts, and the infidelity of the RNA polymerases used for in vitro transcriptions (Boyer and Haenni, *Virology* 198:415–426 (1994)). It is clear that there remains a strong need for an infectious cDNA clone of the rubella virus genome having a higher infectivity than currently available rubella virus clones, and for a recombinant rubella virus vaccine. The isolation of a highly infectious cDNA clone will be useful for the development of a recombinant rubella vaccine vector. A recombinant vaccine vector based on live, attenuated rubella vaccines is also highly desirable in a pediatric setting, where immunization with a recombinant rubella vaccine expression vector can be used to induce immunity against rubella alone, or both rubella and another virus or viruses whose genes may be introduced into the vector. Such vaccine vector is also desirable in an adult patient setting, where a recombinant rubella vaccine is needed that can be safely administered to pregnant and older women without risk of birth defects, auto immune disease, or neurologic symptoms. Thus, rubella virus expression vectors that can be used to produce and develop recombinant vaccines against rubella and other viruses would be highly useful to combat rubella and other diseases in various populations. Also, the development of a method to improve the stability of togavirus expression vectors would be very useful for the development of the expression vectors and recombinant vaccines for rubella virus and other viruses of this family, such as alphaviruses. The instability of alphavirus expression vectors is well known, as reported by Pugachev, K. V., et al., *Virology* 209:155–166 (1995) and Pugachev, K. V., et al., *Virology* 212:587–594 (1995). Futhermore, rubella virus expression vectors would serve as valuable molecular biology tools to study rubella virus and other viruses of the togavirus family.

SUMMARY OF THE INVENTION

There has been a long-standing problem of an inability to produce highly infectious rubella virus clones. Applicants discovered that by replacing a portion of a low infectivity clone with a corresponding fragment that was synthesized by a method known to produce sequences with few mutations, Applicants obtained a chimera exhibiting high infectivity. Therefore, the present invention includes methods of producing highly infectious rubella virus clones by replacing segments of a low infectivity clone with corresponding segments produced by a protocol known to generate sequences having a minimal number of mutations.

Additionally, highly infectious cDNA clones of the rubella virus are provided herein. The clones are chimeric DNA molecule constructs containing portions of a rubella virus cDNA clone having a low specific infectivity and one or more portions of at least one rubella virus genome synthesized by a method known to produce sequences having a minimal number of mutations. The highly infectious rubella virus clones of the invention are useful as molecular biology tools for studying rubella virus and can be useful for developing recombinant vaccines against rubella.

The highly infectious cDNA clones have a specific infectivity greater than 0.5 plaques/µg of transcript. In several preferred embodiments of the invention, the specific infectivities of viral transcripts are approximately $10^4$ plaques/µg of transcript.

In preferred embodiments the cDNA clones are prepared by replacing one or more fragments of a known w-Therien-derived infectious cDNA clone having low specific infectivity with corresponding fragments from an f-Therien rubella virus strain synthesized by a method known to produce sequences having a minimal number of mutations.

Togavirus expression vectors for the expression of live, attenuated togavirus and a foreign gene are also dherein. The expression vector constructs contain a togavirus non-structural protein open reading frame; a first expression element for expression of a heterologous virus; a gene encoding the foreign gene or a multiple cloning site into which the foreign gene may be inserted; a second expression element for the expression of the live, attenuated togavirus; and a togavirus structural protein open reading frame. The togavirus non-structural protein open reading frame and togavirus structural protein open reading frame are preferably from an infectious rubella virus clone. The preferred foreign gene is a heterologous virus. The expression element is either a subgenomic (SG) promoter or an internal ribosome entry site (IRES). Administration of the vector as an immunization agents is useful for the induction of immuity against the togavirus, the heterologous virus, or both. The incorporation of at least one IRES in the vector results in a recombinant virus of improved stability.

In a preferred embodiment, the expression elements for expression of both the foreign gene and the togavirus are SG promoters. A multiple cloning site (MCS) is located between the two SG promoters. The MCS is useful for the insertion of the foreign genes under the control of the upstream SG promoter, including but not limited to reporter genes or heterologous virus genes. Exemplary reporter genes include green fluorescent protein (GFP) or chloramphenicol acetyltransferase (CAT) genes. Exemplary heterologous virus genes include Japanese encephalitis virus genes.

In another preferred embodiment, the second expression element, which controls expression of the togavirus structural protein, is replaced by an internal ribosome entry site (IRES). The IRES is a sequence capable of promoting the entry of a ribosome into an RNA molecule at an internal site, independently of the polyadenylated cap.

This construct is prepared by replacing an indigenous SG promoter of an infectious rubella cDNA clone with the IRES, thus placing the expression of rubella virus structural genes under the control of IRES. Surprisingly, this construct gives rise to viable rubella virus. This recombinant construct is yet another embodiment of the present invention. A duplicate copy of the SG promoter region is then placed into the intermediate construct directly upstream of IRES. A MCS is placed downstream of the SG promoter to allow for the insertion of the foreign genes. Introduction of the IRES element results in improved stability of the recombinant virus, including improved expression of the foreign gene protein.

In the present embodiments, the vectors are prepared using a backbone of an infectious rubella cDNA clone containing portions of both a cDNA clone having a low specific infectivity and a second rubella virus genome Robo302, described herein, and Robo402 described in Pugachev, K. V., et al., (2000) *Virology*, 273, 189–197, incorporated herein by reference in its entirety.

The vectors are useful for the induction of immunity or to develop recombinant vaccines against rubella and/or a heterologous virus whose genes may be inserted into the expression vector. The vectors can also be used to study rubella, particularly rubella virus replication. The method of introduction of an IRES element into an expression vector based on rubella virus, which belongs to togavirus family (Togaviridae), can be used to develop other togavirus expression vectors of improved stability.

It is therefore an object of the present invention to provide a highly infectious cDNA clone of the rubella virus genomic RNA.

It is a further object of the present invention to provide a molecular biology tool for studying rubella, particularly rubella virus replication.

It is a further object of the present invention to provide cDNA clones for the development of a recombinant rubella virus vaccine.

It is another object of the present invention to provide an expression vector based on rubella virus.

It is a further object of the present invention to provide an expression vector based on rubella virus for the expression of protein or proteins whose genes are inserted into the vector.

It is a further object of the present invention to provide an expression vector based on rubella virus for the expression of protein or proteins in eukaryotic cells, including animal cells.

It is a further object of the present invention to provide an expression vector based on rubella virus for the induction of immunity against rubella and/or a different virus or viruses whose genes are inserted into the vector.

It is a further object of the present invention to provide an expression vector based on rubella virus for the development of recombinant vaccines against rubella virus and/or a different virus or viruses whose genes are inserted into the vector.

It is a further object of the present invention to provide an expression vector based on highly infectious cDNA clones of the rubella virus.

It is yet another object of the present invention to provide a viable cDNA rubella clone that contains IRES as one of its promoters.

It is a further object of the present invention to provide an expression vector based on rubella virus having enhanced stability.

It is yet another object of the present invention to provide a molecular biology tool to study rubella, including but not limited to rubella virus replication and protein expression.

It is yet another object of the present invention to provide a molecular biology tool to study the function of IRES elements in the context of a togavirus genome.

It is yet another object of the present invention to provide a molecular biology tool to study togaviruses other than rubella, in particular their replication and protein expression, by means of introducing IRES elements into their genome.

DETAILED DESCRIPTION OF THE INVENTION

Figure 1:
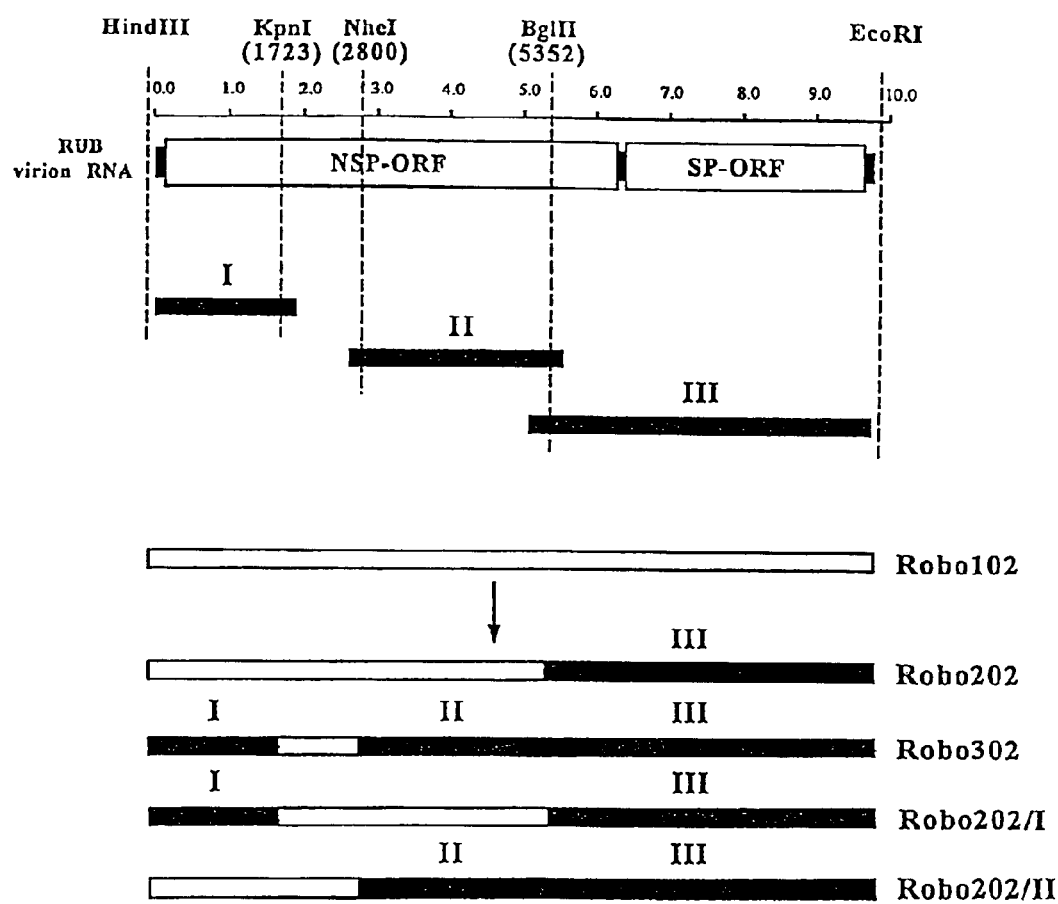
FIG. 1 is a schematic diagram showing modifications to the construct Robo102 (w-Therien) to produce highly infectious chimeric construct clones, Robo202, Robo302, Robo202/I and Robo202/II.
Figure 2:
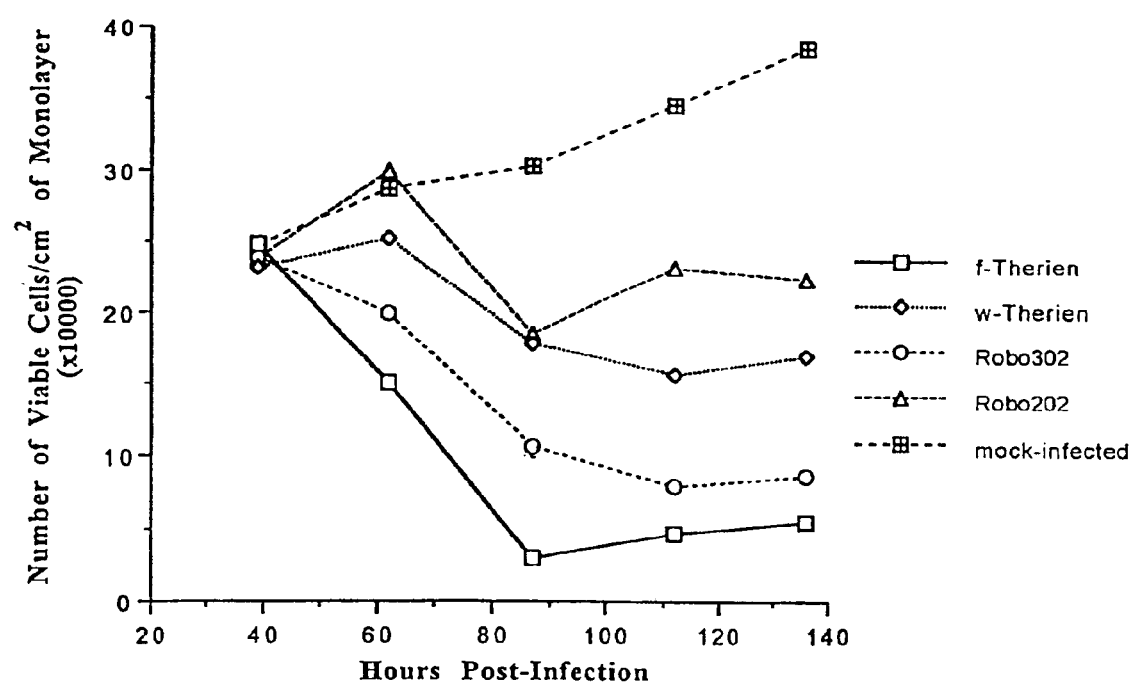
FIG. 2 is a graph comparing the infectivity of the Robo302 and Robo202 constructs with the f-Therien rubella virus strain, the w-Therien rubella virus strain, and a mock-infected control.

There has been a long-standing problem of an inability to produce highly infectious rubella virus clones. Applicants discovered that, by replacing a portion of a low infectivity clone with a corresponding fragment that was synthesized by a method known to produce fragments with few mutations, Applicants obtained a chimera exhibiting high infectivity. Therefore, the present invention includes methods of producing highly infectious rubella virus clones by replacing segments of a low infectivity clone with corresponding segments produced by a protocol known to generate sequences having a minimal number of mutations.

Also disclosed are highly infectious, isolated cDNA clones of rubella virus. The infectious rubella virus clones are useful as molecular biology tools for studying rubella virus and for developing recombinant vaccines against rubella.

The term "highly infectious cDNA clone" is defined herein as a cDNA clone having a high specific infectivity, which is defined as a specific infectivity of greater than 0.5 plaques/µg of transcript. The term "low infectivity" or "low specific infectivity" is defined herein as a specific infectivity of less than or equal to 0.5 plaques/µg of transcript.

The highly infectious, isolated cDNA molecules are inserted into a vector that enables replication of the nucleotide sequence of the molecules. A preferred vector is a bacterial plasmid such as pUC 19, pGEM, or PBR-322 (all available from Promega Biotec, Madison, Wis.) or pC11921 adjacent to a bacteriophage RNA polymerase promoter sequence such as the SP6 RNA polymerase (Promega Biotec) such that RNA copies of the rubella virus DNA can be synthesized in vitro. The vector is chemically introduced into susceptible culture cells, for example, $E.\ coli$, for amplification and production of large amounts of the cDNA clone. For use, the purified infectious clone is restricted with a restriction endonuclease such as Nsi 1 (New England Biolabs, Beverly, Mass.) for linearization at the termination of the rubella virus cDNA sequences. The linearized plasmid is then transcribed with an RNA polymerase such as SP6 RNA polymerase, which results in production of RNA transcripts templated from the rubella virus cDNA sequence in the non-pathogenic infectious clone.

In preferred embodiments of the present invention, the rubella virus clones have specific infectivities of approximately $10^4$ plaques/µg of transcript. In these preferred embodiments, the rubella virus cDNA clones contain portions of a cDNA clone having a low specific infectivity of approximately 0.5 plaques/ug of transcript or less. In the preferred embodiment, the cDNA clone having a low specific infectivity is the clone described by Wang, et al., *J. Virol.* 68:3550–3557 (1994), having the sequence shown in SEQ ID NO:1.

The chimeric constructs also contain portions, or fragments, of cDNA from a rubella virus genome in which the cDNA fragments have been produced in a manner known to generate sequences having a minimal number of mutations. The highly infectious constructs are prepared by replacing one or more portions of the cDNA clone having low infectivity with corresponding DNA fragments having fewer mutations. The corresponding DNA fragments may be derived from any rubella virus strain. The specific infectivities of the cDNA clones of the present invention exhibit an increase of at least $10^4$ fold over infectivity of a cDNA clone derived solely from a strain known to have a low specific infectivity.

Rubella Genome Fragments Conferring High Infectivity

Rubella genome fragments that confer the highly infectious property upon the chimera are those produced in a manner known to generate sequences having a minimal number of mutations. The fragments that confer the highly infectious property are obtained as follows. w-Therien, f-Therien and other rubella virus genomes are available from laboratories specializing in rubella virus research. Rubella virus genomes may also be obtained by drawing blood from a person or animal infected with the rubella virus and isolating the genomes by methods that are standard in the art. Such methods can be found in standard lab manuals.

Any rubella virus strains that are or may become available can be used to produce a fragment using a protocol known to generate sequences having a minimal number of mutations. No specific rubella virus genome need be used as a template for the DNA fragments because any rubella virus genome will achieve the desired result. Possible DNA fragments include those derived from the original genome from which the low infectivity clone was produced, as long as the DNA fragments have been produced by a protocol known to generate sequences having a minimal number of mutations.

The fragments can then used for replacing a corresponding fragment of rubella virus clones having a specific infectivity of less than or equal to 0.5 plaques/µg of transcript. Materials and protocols for replacing regions of a cDNA clone with a replacement region are standard in the art. No special materials or protocols are required. Protocols can be found in standard laboratory manuals, such as Sambrook et al., *Molecular Cloning: A Laboratory Manual*, second edition, Cold Spring Harbor Laboratory Press, New York (1989). Materials can be purchased from widely used and well-known companies, such as, Sigma Chemical, Inc., Promega, and New England Biolabs.

In the most preferred embodiments of the present invention, the cDNA clone having a low specific infectivity is derived from the w-Therien rubella virus strain and the cDNA fragments used to replace portions of the cDNA clone are derived from the f-Therien rubella virus strain. Most preferably, the chimeric constructs contain one or more portions of the infectious cDNA clone Robo102, derived from the w-Therien rubella virus strain, as described in Wang, et al., *J. Virol.* 68:3550–3557 (1994), and in U.S. patent application Ser. No. 08/459,041, now U.S. Pat. No. 5,663,065, which is incorporated by reference herein (and shown in SEQ ID NO:1), and one or more fragments of synthesized cDNA having few mutations and derived from the f-Therien rubella virus strains.

Any method for producing corresponding DNA fragments having a minimal number of mutations may be used to make the clones of the present invention. Three preferred fragments derived from f-Therien are fragment III (SEQ ID NO:10), fragment I (SEQ ID NO:2), and fragment II (SEQ ID NO:3).

Preferably, the cDNA fragments are created using the technique known by those skilled in the art as reverse transcriptase-long polymerase chain reaction (RT-long PCR) or high-fidelity long PCR, which allows for the amplification of long nucleic acid sequences. This use of this technique results in a reduction of the number of mutations in the genomic cDNA. High-fidelity long PCR amplification of rubella virus cDNA fragments is achieved with first strand cDNA synthesis, using currently available nucleic acid synthesis kits such as the RiboClone cDNA Synthesis System kit (Promega Corporation, Madison, Wis.) according to the protocol of the manufacturer, followed by PCR amplification. In a preferred embodiment, a high-fidelity DNA polymerase, such as ExTaq polymeraserom PanVera Corp., which has a proofreading capacity, is employed for PCR amplification. Exemplary oligonucleotide primers for the generation of nucleic acid fragments, with which to replace the portions of the cDNA clone having low infectivity, are set forth in the Examples below.

Other methods of producing fragments that generate sequences having a minimal number of mutations may become available in the future.

By employing the method of the present invention on a low infectivity rubella virus clone, Applicants discovered that some type of error or mutations in a particular region may cause low infectivity of a rubella virus clone. As discussed in more detail in Example 2, Applicants discovered the deleterious regions in Robo 102 by inserting three different fragment DNAs into three corresponding regions of Robo 102. Insertion of fragment I or fragment II, individually, did not increase the infectivity of subsequently produced viral transcripts. However, the replacement of fragment III into Robo102 did result in increased infectivity. This method may be used on other low infectivity clones to determine if specific locations are the cause of low infectivity.

The following steps may be followed to prepare a highly infectious rubella virus clone of the invention from a low infectivity clone. A low infectivity DNA molecule clone may be obtained by the method described in Wang, et al., *J. Virol.* 68:3550–3557 (1994). A copy of a rubella virus genome may be obtained from a laboratory specializing in this area, or from the American Type Culture Collection, or isolated from a person infected with the disease. DNA fragments of the genome may be synthesized by a method known to produce sequences having a minimal number of mutations for substitution into the DNA molecule encoding an infectious rubella virus having low infectivity. Portions of the low infectivity clone are then replaced with the newly synthesized corresponding fragments to obtain a chimeric construct exhibiting high infectivity.

As shown in FIG. 1, in a preferred embodiment of the present invention, the 5' end portion of the cDNA clone having low specific infectivity (the w-Therien derived Robo102 construct, SEQ ID NO:1) is replaced with the corresponding cDNA fragment (fragment III) from a second rubella virus genome (the f-Therien strain of the rubella virus genome), to create a highly infectious construct (Robo202). The nucleic acid sequence of fragment III is set forth in the sequence listing as SEQ ID NO:10. Fragment III contains the entire structural protein open reading frame region (SP-ORF) of the genome. The structural protein open reading frame encodes at least three structural proteins, C, E1 and E2. Fragment III also contains a portion of the 5'-end of the non-structural protein open reading frame (NSP-ORF) and the entire structural protein open reading frame (SP-ORF). Fragment III is also described as a nucleic acid molecule between restriction endonuclease cleavage sites EcoRI and BglII. More specifically, the Robo202 chimeric construct includes nucleotides 1 to approximately 5352 of SEQ ID NO:1 and replaces nucleotides 5353 to 9734 of SEQ ID NO: 1 with the corresponding sequence from the f-Therien rubella virus genome.

In another preferred embodiment of the present invention, three fragments from a second rubella virus genome (the f-Therien rubella virus genome), are used to replace the corresponding fragments of the infectious rubella virus cDNA clone having low specific infectivity (Robo102) to create a chimeric construct having high specific infectivity (Robo302). As shown in FIG. 1, the first fragment (fragment I) contains the 3' end of the non-structural open reading frame. Fragment I is also described as the nucleic acid molecule between restriction endonuclease cleavage sites HindIII and KpnI. The nucleic acid sequence of fragment I is set forth in the sequence listing as SEQ ID NO:2. The second fragment (fragment II) contains most of the 5' end of the non-structural open reading frame (NSP-ORF). Fragment II is also described as the nucleic acid molecule between restriction endonuclease cleavage sites NheI and BglII. The nucleic acid sequence of fragment II is set forth in the sequence listing as SEQ ID NO:3. Fragment III (SEQ ID NO:10), also replaces the corresponding fragment in Robo102. In particular, fragment I (SEQ ID NO:2) replaces nucleotides 1 to 1723 of Robo102, fragment II (SEQ ID NO:3) replaces nucleotides 2800 to 5352 of Robo102, and fragment III (SEQ ID NO:10) replaces nucleotides 5353 to 9734 of Robo102. The resulting construct, Robo302, contains roughly 90% of the f-Therien rubella virus genome and 10% of the w-Therien strain of the rubella virus genome.

In another preferred embodiment of the present invention, fragments I (SEQ ID NO:2) and III replace the corresponding portions of the infectious cDNA clone having low infectivity (Robo102) to produce a highly infectious cDNA clone (Robo202/I). As shown in FIG. 1, the resulting cDNA construct contains both the 5' and 3' ends of the f-Therien strain of the rubella virus genome corresponding to nucleotides 1 to 1723 and 5352 to 9734, respectively. The central portion of the Robo202/I cDNA is derived from nucleotides 1723 to 5352 of the w-Therien strain.

In another preferred embodiment of the present invention, fragments II (SEQ ID NO:3) and III as described above, replace the corresponding portions of the infectious cDNA clone having low infectivity (Robo102) to produce a highly infectious cDNA clone (Robo202/II). As shown in FIG. 1, the resulting cDNA construct contains the 5' end of the w-Therien rubella virus genome up to nucleotide 2800 with the remaining section consisting of the f-Therien rubella virus genome.

The specific infectivity of highly infectious clones Robo 202, Robo 302, Robo 202/I, and Robo 202/II is approximately $10^4$ plaques per µg. As a comparison, the specific infectivity of the rubella virus RNA is $10^5$ plaques per µg.

Recombinant togavirus expression vector constructs are described herein. The vectors are useful for protein expression in vitro or in vivo, induction of immunity, or for development recombinant vaccines against rubella and/or a heterologous virus whose genes may be inserted into the expression vector. The expression vectors can also be used as molecular biology tools to study togaviruses, particulary rubella viruses, more particularly rubella virus replication and protein expression. The vectors can also be used to study the function of IRES elements in the context of a togavirus genome. The method of incorporating IRES elements into the rubella virus expression vectors can be used to study togaviruses other than rubella, particularly their replication and protein expression.

The expression vector constructs contain a togavirus non-structural protein open reading frame; a first expression element for expression of a heterologous virus; a gene encoding the foreign gene or a multiple cloning site into which the foreign gene may be inserted; a second expression element for the expression of the live, attenuated togavirus; and a togavirus structural protein open reading frame. The togavirus non-structural protein open reading frame and togavirus structural protein open reading frame are preferably from an infectious rubella virus clone. The preferred foreign gene is a heterologous virus gene. The expression element is either a subgenomic (SG) promoter or an internal ribosome entry site (IRES). The incorporation into the vector of at least one IRES results in a recombinant virus of improved stability. Administration of the vector as an immunization agent is useful for the induction of immunity against the togavirus, the heterologous virus, or both.

The term "improved stability" is defined herein as the ability to maintain the expression of foreign genes by the recombinant virus for longer than three passages through the cell culture, wherein the recombinant virus results from the infection of cells by the virus expression vector.

The term "foreign gene" as used herein means a heterologous gene whose expression by the expression vector described herein is desirable.

In a preferred embodiment, the expression elements for expression of both the foreign gene and the togavirus are SG promoters. A multiple cloning site (MCS) is located between the two SG promoters. The MCS is useful for the insertion of the foreign genes under the control of the upstream SG promoter, including but not limited to reporter genes or heterologous virus genes. Exemplary reporter genes include green fluorescent protein (GFP) or chloramphenicol acetyltransferase (CAT) genes. Exemplary heterologous virus genes include encephalitis virus, hepatitis and Dengue virus genes.

In another preferred embodiment, the second expression element, which controls expression of the togavirus structural protein, is replaced by an internal ribosome entry site (IRES). The IRES is a sequence capable of promoting the entry of a ribosome into an RNA molecule at an internal site, independently of the polyadenylated cap This construct is prepared by replacing an indigenous SG promoter of an infectious rubella cDNA clone with the IRES, thus placing the expression of rubella virus structural genes under the control of IRES. Surprisingly, this construct gives rise to viable rubella virus. This recombinant construct is yet another embodiment of the present invention. A duplicate copy of the SG promoter region is then placed into the intermediate construct directly upstream of IRES. A MCS is placed downstream of the SG promoter to allow for the insertion of the foreign genes. Introduction of the IRES element results in improved stability of the recombinant virus, including improved expression of the foreign gene protein.

In the present embodiments, the vectors are prepared using a backbone of an infectious rubella cDNA clone containing portions of both a cDNA clone having a low specific infectivity and a second rubella virus genome, such as Robo302, described herein, or Robo402 described in Pugachev, K. V., et al., (2000) *Virology,* 273, 189–197, incorporated herein by reference in its entirety, or a combination of the two clones.

The expression vector is constructed using an infectious rubella cDNA clone and modifying its subgenomic promoter-containing site. The molecular biology techniques employed to perform such modifications are well-known to the one skilled in the art and are detailed in such common in the art manuals as Sambrook, J., Fritsch, E. F., and Maniatis, T. *Molecular Cloning: A Laboratory Manual, $2^{nd}$ ed.* Cold Spring Harbor Laboratory Press, Plainview, N.Y. (1989). A preferred starting cDNA clone is a chimeric DNA construct based on a bacterial plasmid such as pUC 19, pGEM, or PBR-322 (all available from Promega Biotec, Madison, Wis.) containing a cDNA copy of a viral genome positioned adjacent to an RNA polymerase promoter, such as an the SP6 RNA Polymerase (Promega Biotec) such that infectious in vitro transcripts can be synthesized. The most preferred cDNA clone is a highly infectious cDNA clone such as wild-type Therien strain rubella infectious clone Robo302 described herein, or Robo402 described in Pugachev, K. V., et al., (2000) *Virology,* 273, 189–197, incorporated herein by reference in its entirety.

In the preferred embodiments of the present invention, the subgenomic (SG) promoter containing site of a cDNA rubella virus clone is modified to contain, between a non-structural-protein open reading frame (ORF) and structural protein ORF, a promoter followed by restriction nuclease recognition (cloning) site or sites that may be used to introduce a foreign gene, including but not limited to reporter genes, such as green fluorescent protein or chloramphenicol acetyltransferase, and heterologous virus, such as Japanese encephalitis virus, genes. The subgenomic structural protein genes of rubella virus either remain under the control of another promoter, such as the indigenous subgenomic promoter, or an internal ribosome entry site. For use, the vector is chemically introduced into susceptible culture cells, for example, *E. coli,* for amplification and production of large amounts of the cDNA clone. For use, the purified infectious clone is restricted with a restriction endonuclease such as EcoRI (New England Biolabs, Beverly, Mass.) for linearization at the termination of the rubella virus cDNA sequences. The linearized plasmid is then transcribed in vitro with an RNA polymerase such as SP6 RNA polymerase, which results in production of RNA transcripts. The resulting RNA transcripts are used to transfect the cells by transfection procedures known to those skilled in the art. The cells, in turn, will produce both the native structural proteins of the rubella virus and the protein encoded by the foreign gene. The replication of the RNA sequences and the expression of the encoded protein by the cells may be monitored by various means known to the ones skilled in the art. The cells will further produce recombinant virus particles which, in turn, may be used to infect cells or organisms.

When an appropriate amount of the infectious clone RNA transcript is transfected into susceptible cells by transfection procedures known to those skilled in the art, less virulent togavirus is recovered from the culture fluid within several days incubation. The identity of the virus recovered from the transfected cells can be confirmed by sequencing a specific region of the infectious clone in which a mutation exists which distinguishes it from the wild-type virus.

The less virulent togavirus is then combined with a pharmaceutically acceptable carrier to provide a safe, effective vaccine, such as a rubella virus vaccine. The carrier can be oil, water, saline, phosphate buffer, polyethylene glycol, glycerine, propylene glycol, and combinations thereof, or other vehicles routinely used by the pharmaceutical industry for these purposes. The vaccine is usually provided in lyophilized form and therefore is free of preservatives.

It will be understood by those skilled in the art that modified cDNA for other DNA or RNA viruses could be inserted into the vector in combination with the rubella virus cDNA to make a vaccine effective in immunizing a patient against more than one virus. For example, the modified cDNA of RNA viruses such as encephalitis, hepatitis or Dengue fever virus, is inserted into the vector to produce a combined recombinant vaccine, particularly Japanese encephalitis or hepatitis C virus.

The vaccine can be administered by any appropriate route, for example, orally, parenterally, intravenously, intradermally, intramuscularly, subcutaneously, or topically, in liquid or solid form, in a single dose or a dose repeated after a certain time interval. Preferably, the administration of the vaccine will result in in vivo protein expression of the proteins encoded by the open reading frames contained in the expression vector construct. Most preferably, the administration of the vaccine will result in the induction of immunity against the viruses whose proteins are encoded by the open reading frames. The vaccine is preferably administered subcutaneously at a concentration range from $10^2$ to $10^4$ TCID$_{50}$/person. (TCID is an abbreviation for tissue culture infectious doses). Preferably, the vaccine is provided to the physician in a lyophilized form, reconstituted in an appropriate solvent such as deionized water or saline, and administered as a single injection.

Expression Vector Construction

Figure 4:
FIG. 4 is a schematic diagram showing genomic arrangements of the rubella constructs Robo302, Robo402, dsRobo302, Robo402/IRES.
Figure 4:
Figure 4:
Figure 4:
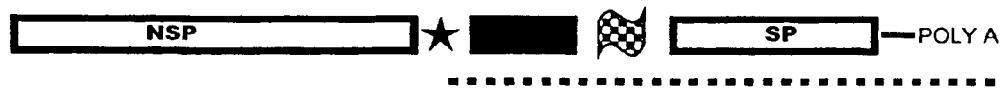

In a preferred embodiment of the present invention, a rubella expression vector is constructed using the wild-type Therien strain rubella infections clone Robo302 described herein. As shown in FIG. 4, an additional SG promoter is located between the non-structural protein and structural protein ORFs. The production of alphavirus (other members of togavirus family) expression vector constructs from infectious clones of alphaviruses by duplicating the subgenomic promoter is described by Bredenbeek P., et al., *J. Virol.* (1993); Liljestrom P., et al. *Bio/Technology* (1991), Smerdou C., et al., *J. Virol.* (1999); et. al. *Virology* (1997); and Schlesinger S. et al. *Curr. Opin. Biotechnol.* (1999).

In the alphavirus-based vectors, the second SG promoter is placed both between the ORFs and downstream of the SP-ORF within the 3' untranslated region, which is 400 to 500 nucleotides long in these viruses. In the vectors described herein, the region between the structural and non-structural protein ORFs, rather than the region downstream of the structural protein ORF (3' untranslated region), was chosen for the location of the additional SG promoter because the rubella virus 3' untranslated region is relatively short (60 nucleotides) and the 3' 300 nucleotides (including the 3' end of the structural protein ORF) appear to be necessary for efficient virus replication, as reported by Chen, et al., *J. Virol.* 73:3386–3403 (1999).

As the rubella SG promoter has not been mapped, a region consisting of the 3'-terminal 126 nucleotides of the non-structural protein ORF (NSP-ORF) and the entire 120-nt noncoding region between the NSP-ORF and the SP-ORF is duplicated. A multiple cloning site (MCS) containing convenient restriction sites (including unique sites for restriction endonucleases XbaI, BstBI, HpaI, and NsiI, all available from New England Biolabs, Beverly, Mass.) is located between the SG promoters for insertion of foreign genes. Thus, in this construct the SG RNA transcribed from the upstream SG promoter is translated to produce the foreign gene that may be placed in MCS, while the SG RNA transcribed from the downstream SG promoter is equivalent to the standard SG RNA and is translated to produce the virus structural proteins. The plasmid is termed dsRobo302.

In another preferred embodiment, an IRES element is incorporated into the rubella expression vector in place of the second SG promoter. Construction of this vector is initiated by replacing the SG promoter with the IRES in Robo402. Surprisingly, transcripts from this construct, Robo402/IRES, shown in FIG. 4, give rise to viable virus which formed plaques on Vero cells but do not produce subgenomic RNA. This shows that an IRES element can drive expression of a togavirus structural protein even in the absence of SG promoter or the corresponding subgenomic RNA.

In another preferred embodiment, the non-structural protein ORF is followed by a SG promoter followed, in turn, by the MCS for the introduction of foreign genes, such as the gene for the green fluorescent protein gene (GFP), followed by an IRES element, followed by the structural protein ORF. In this particular embodiment, the construct is developed from the intermediate construct Robo402/IRES. This expression vector results in a virus of improved stability when passaged multiple times through the Vero cells compared to dsRobo302.

Modifications and variations of the DNA encoding an infectious rubella virus and rubella virus expression vectors, methods of making and use thereof, methods of making a less virulent rubella virus and use thereof, an improved rubella virus vaccine and methods making and use thereof are intended to come within the scope of the present invention.

The foregoing invention will be further understood with reference to the following non-limiting examples.

EXAMPLE 1

Preparation of f-Therien Virion RNA and RT-long PCR

Vero cells (ATCC, Rockville, Md.) were infected with f-Therien rubella virus (multiplicity of infection (m.o.i.)= 0.5). Four days post infection, culture medium was harvested and PEG-precipitated virion RNA was isolated using either TRI-Reagent LS (Molecular Research Center, Cincinnati, Ohio), according to the protocol provided by the manufacturer, or by using the method described by Wang, C. Y. et al., *J. Virol.* 68:3550–3557 (1994). The extracted RNA was further purified by oligo-(dT)-cellulose chromatography, redissolved in 50 µl of water, and stored at −70° C.

First strand cDNA synthesis was performed with AMV reverse transcriptase (RiboClone™ cDNA Synthesis Kit; Promega, Madison, Wis.), according to the protocol provided by the manufacturer, in the presence of sodium pyrophosphate with one of the following three primers:

SEQ ID NO:4:
5'-GGGAAGCTTGCACGACACGGACAAAAGCC
(underlined sequence is complementary to nucleotides 1897–1916 of the rubella virus genome); or SEQ ID NO:5: 5'-TAGTCTTCGGCGCAAGG
(complementary to nucleotides 5744–5760 of the rubella virus genome); or
SEQ ID NO:6:
5'-CGCGAATTC(T)$_{20}$CTATACAGCAACAGGTGC
(contains an EcoRI site (double underlined), a (dT)$_{20}$-stretch, and a sequence complementary to nucleotides 9740–9757 of the rubella virus genome (single underlined)).

Three large cDNA clones were then generated using the PCR techniques described by Barnes, W. M., et al., *Proc. Natl. Acad. Sci. USA* 91:2216–2220 (1994) and Cheng, S., et al., *Proc. Natl. Acad. Sci. USA* 91:5695–5699 (1994), the teachings of which are incorporated by reference herein. The single-stranded products, Fragments I (SEQ ID NO:2), II (SEQ ID NO:3), and III were phenol-chloroform extracted and precipitated twice with ethanol, first in the presence of 2M ammonium acetate and second in the presence of 0.3 M sodium acetate. The precipitates were redissolved in 10 μg of water and 2 to 5 μl were used in 50 μl PCR reactions that contained 2.5 units of ExTaq temperature stable DNA polymerase (TaKaRa LA PCR kit, Pan Vera Corp., Madison, Wis.), and the following three primers:

SEQ ID NO:7:

5'-TCGAAGCTTATTTAGGTGACACTATAGCAATG
GAAGCTATCGGACCTCGCTTAGG (contains a HindII site (double underlined), the SP6 RNA polymerase promoter (dot underlined), and nucleotides 1–28 of the rubella virus genome (single underlined));
SEQ ID NO:8:
5'-TTTGCCAACGCCACGGC
(containing nucleotides 2600–2616 of the rubella virus genome); and
SEQ ID NO:9:
5'-AGCTCACCGACCGCTAC
(containing nucleotides 5319–5335 of the rubella virus genome).

The following primers and amplification protocols were utilized: for fragment I, the primer set forth in SEQ ID NO:7 served as a primer for 30 cycles of 20 seconds at 98° C., one second at 55° C. and three minutes at 70° C.; for fragment II, the primer set forth in SEQ ID NO:8 served as a primer for 30 cycles of 20 seconds at 98° C., one second at 50° C., and five minutes at 70° C.; and for fragment III, the primer set forth in SEQ ID NO:9 served as a primer for 30 cycles of 20 seconds at 98° C., one second at 52° C., and seven minutes at 68° C. These techniques were slightly modified by the addition of 10% DMSO to the PCR amplifications due to the high G+C content of the rubella genome. Roughly ten percent of the rubella virus genome between fragments I (SEQ ID NO:2) and II (SEQ ID NO:3) could not be amplified from the virion RNA, presumably due to peculiarities of secondary and or tertiary structure in this region.

Using standard recombinant DNA techniques, fragments I (SEQ ID NO:2), II (SEQ ID NO:3), and III were digested with the restriction enzymes HindIII and KpnI, NheI and BglII, or BglII and EcoRI, respectively, as described below, and individually ligated with Robo102 from which the corresponding fragment had been removed. Phenol-chloroform extracted and linearized constructs were transcribed in vitro as described in Pugachev, K. V., P. W. Mason, and T. K. Frey *Virology* 209:155–166 (1995), using SP6 RNA polymerase (Epicentre Technologies, Madison, Wis.) in the presence of a cap structure analog, and transfected into Vero cells using lipofectin-mediated techniques described by Rice et al., *New Biol.* 1:285–296 (1989).

Freshly linearized Robo plasmids in the presence of the m7G(5')ppp(5')G cap structure analog (New England Biolabs, Beverly, Mass.) were used in the transcription reactions in accordance with the method of Rice et al., New Biol. 1:285–296 (1989), with the modification that Opti-MEMI-reduced serum medium replaced phosphate buffered saline (PBS) during transfection. Transfected cells were incubated and tested for rubella induced cytopathic effects.

As shown in FIG. 1, the construct containing fragment III was designated Robo202, the construct containing fragments I (SEQ ID NO:2), II (SEQ ID NO:3), and III was designated Robo302, the construct containing fragments I (SEQ ID NO:2) and III was designated Robo202/I, and the construct containing fragments II (SEQ ID NO:3) and III was designated Robo202/II.

EXAMPLE 2

Construction and Specific Infectivity of Robo202

The specific infectivity of the rubella virus cDNA clone designated Robo202, as described above in Example 1, was determined as follows. After PCR amplification of fragment III (SEQ ID NO:10), as described above, the fragment was digested with restriction enzymes BglII and EcoRI and ligated with a similarly digested Robo102 clone, as shown in FIG. 1. In vitro transcription of the newly constructed clone, Robo202, and subsequent transfection into Vero cells resulted a $10^4$-fold increase in infectivity. While the slightly infectious Robo102 clone did not induce cytopathic effects within eight days after transfection into Vero cells, insertion of fragment III into the Robo102 clone resulted in cytopathic effects within five days of transfection into Vero cells. However, insertion of either fragment I (SEQ ID NO:2) or fragment II (SEQ ID NO:3) produced viral transcripts, and therefore the mutation that caused low infectivity of Robo102 is believed to be located in the region replaced by fragment III.

EXAMPLE 3

Construction and Specific Infectivity of Robo302

Following PCR amplification of fragments I (SEQ ID NO:2) and II (SEQ ID NO:3), the fragments were digested with restriction enzymes HindIII and KpnI, and NheI and BglII, respectively. The fragments were simultaneously inserted into a Robo202 clone wherein the corresponding fragments had been removed, resulting in the Robo302 construct, as shown in FIG. 1. The addition of fragments I (SEQ ID NO:2) and II (SEQ ID NO:3) to the Robo202 construct, produced viral transcripts with an increased specific infectivity.

Vero cells grown in 24-well plates were infected with the indicated viruses at an m.o.i. of 2 pfu/cell. At indicated times post infection, cells were trypsinized, washed with PBS and stained with trypan blue. Three aliquots of each trypsinized cell suspension were counted. As shown in FIG. 2, viral transcripts derived from the Robo302 clone induced approximately 80% cell death over the control, whereas viral transcripts derived from the Robo202 clone resulted in approximately 40% cell death. These results also paralleled the results of plaque assays wherein the Robo302 clone displayed a clear plaque phenotype, and the Robo202 clone displayed an opaque plaque phenotype.

EXAMPLE 4

Construction and Specific Infectivity of Robo202/I and Robo202/II

Fragments I (SEQ ID NO:2) and II (SEQ ID NO:3) were excised from the Robo302 construct with the appropriate restriction enzymes, and introduced individually to produce the Robo202/I and Robo202/II constructs, respectively. Introduction of either fragment resulted in decreased plaque opacity, with Robo202/II producing the most clear plaques, slightly smaller than the plaques produced by Robo302.

EXAMPLE 5

Growth Kinetics of Robo Constructs

Figure 3:
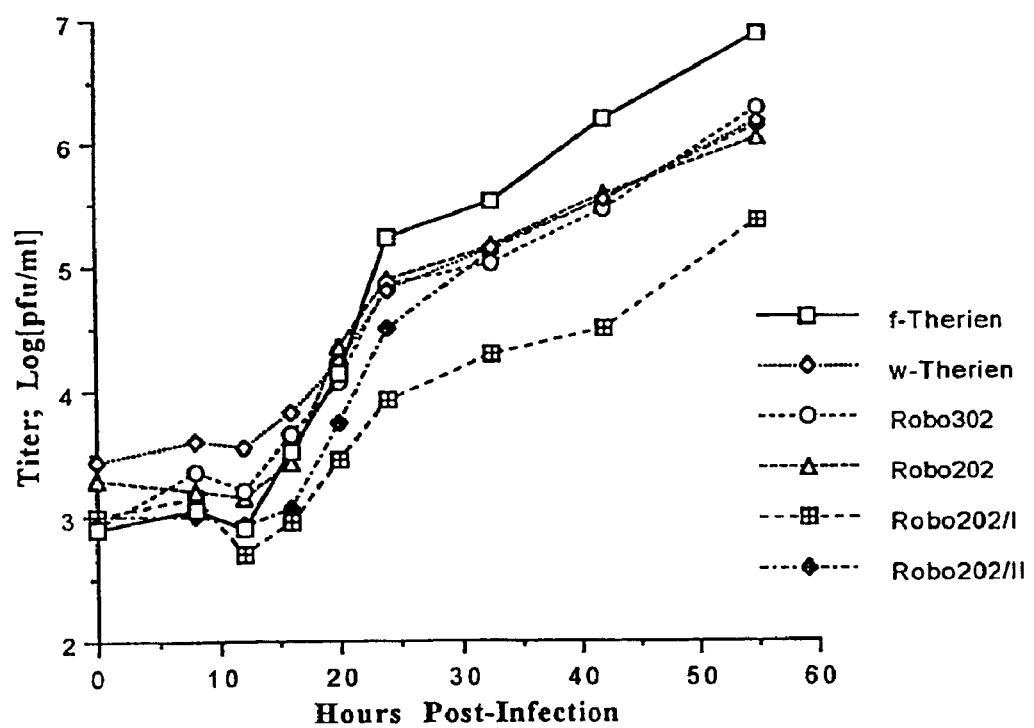
FIG. 3 is a graph comparing the growth curves of the two parent strains, w-Therien and f-Therien, with the four modified constructs, Robo202, Robo302, Robo202/I and Robo202/II, after infection of Vero cells at an m.o.i. of 2 pfu/cell. The graph shows average values of titers produced in two independent experiments.

To elucidate the basis of the difference in plaque phenotype between the Robo constructs, growth curves of the resulting viruses and their ability to kill infected cells were investigated. Because of the limited titer to which one of the viruses, Robo202/I, replicated, an m.o.i. of 2 pfu/cell was used in these experiments. As shown in FIG. 3, the growth kinetics of all of the viruses were similar with a lag phase of roughly 0–12 hours post infection, an exponential phase between 12 and 24 hours post infection, and a slower exponential phase through 55 hours post infection. While f-Therien produced the highest titers, w-Therien, Robo302, Robo202, and Robo202/II produced similar intermediate titers. Robo202/I virus grew to noticeably lower titers than the other viruses. Over a more prolonged course of infection (4 days), w-Therien titers caught up with f-Therien titers, Robo202, Robo302 and Robo202/II titers were approximately two fold lower than f- and w-Therien titers, whereas Robo202/I titers were 8–18 fold lower than any of the other viruses.

To analyze molecular differences between these viruses that could account for the difference in plaque morphology/cell killing, virus macromolecular synthesis was characterized. Production of the rubella virus-specific RNAs (of both positive and negative polarity) was examined by northern hybridization of total intracellular RNAs extracted from infected cells with the result that all of these viruses produced equivalent amounts of all the virus RNA species (data not shown). Non-structural and structural protein synthesis was analyzed by immunoprecipitation of the proteins from lysates of infected cells radiolabeled for 1.5 hours. As shown in FIG. 3, structural protein synthesis was similar for all of the viruses. However production of the non-structural proteins was higher in cells infected with the more cytopathic viruses (f-Therien and Robo302) than the less cytopathic viruses (w-Therien and Robo202). Robo 202/I also produced more non-structural proteins in comparison with Robo202/II. These differences were not due to differences in the number of infected cells in the culture since at 40 hours post infection, a similar percentage of cells (roughly 60%) was infected with f-Therien, w-Therien, Robo302, Robo202 and Robo202/II viruses as determined by indirect immunofluorescence. However, in Robo202/I infected cells, only 35% of cells were infected, probably due to the slower replication rate of this virus.

EXAMPLE 6

Preparation of dsRobo302 Construct

As shown in FIG. 4 Robo302 (reference) contains the standard virus genome with its modular non-structural protein and structural protein ORFs. The region of the Robo302 genome containing the putative SG promoter, nucleotides 6260 to 6506, was duplicated by PCR (polymerase chain reaction); two amplicons (PCR-amplified DNA fragments) were produced, the first using primers 106 and K1, shown in Table 1, and the second using primers K3 and 1, also shown in Table 1. The upstream primer (U) sequence is at the 5' end of the amplicon with respect to the RUB genomic construct; the sequence of RUB nucleotides is thus colinear with the genomic sequence. The downstream primer (D) sequence is at the 3' end of the amplicon with respect to the RUB genomic construct; the sequence of RUB nucleotides is thus complementary with the genomic sequence. In Table 1, nucleotides in the primers containing RUB sequences are underlined; those in the genome (numbered from the 5' end) to which the nucleotides in the primer are colinear or complementary are given in parentheses. Restriction site sequences in the primer used for cloning and the corresponding name are in bold. In the case of primer K3, used to create the MCS in dsRobo302, several restriction sites are present; they are alternately shown in bold and all italics.

Following digestion of amplicon 1 with BglII and XbaI and amplicon 2 with XbaI and AscI, the fragments were inserted simultaneously by means of three-fragment ligation, into Robo302 digested with BglII and AscI (which removed the corresponding fragment from Robo302). This resulted in a rubella virus construct which containes a subgenomic promoter directly downstream of the non-structural gene ORF, followed by multiple cloning site introduced by primer K3, followed by the second subgenomic promoter and structural protein ORF. When in vitro transcripts from dsRobo302 were used to transfect Vero cells (ATCC, Rockville, Md.), virus was recovered. Production of in vitro transcripts from the plasmids and subsequent transfection of Vero cells were done according to standart procedures as described in Pugachev, K. V., et al., *J. Virol.* 71:562–568 (1997).

TABLE 1

PCR primer pairs used in vector construction[a]

| Primer | Sequence[b] | Restriction site(s)[c] |
|---|---|---|
| SG promoter duplication | | |
| Amplicon I | | |
| 106 (U) | agctcaccgaccgctac (5319–5335) (SEQ ID NO:10) | |
| K1 (D) | GCCTCTAGA ttcgggcaccct ggggctct (6488–6507) (SEQ ID NO:11) | *XbaI* |
| Amplicon II | | |
| K3 (U) | GAATCTAGA*GGCC***TTC** GAA*CGC***GTTAAC***ATGC* *AT*gtcctcgctatcgt gcgcgaa (6260–6280) (SEQ ID NO:12) | *XbaI*, *StuI*, *BstBI*, *MluI*, *HpaI*, *NsiI/Ppu10I* |
| 1 (D) | GAAGCGGATGCGCCAA GG (7323–7340) (SEQ ID NO:13) | |
| Robo402/IRES construction | | |
| Amplicon I (EMCV IRES) | | |
| IR-5 (U) | CACAATGCATAATTCC GCCCCTCTCCCTC (SEQ ID NO:14) | *NsiI* |
| IR-3 (D) | CATGGTTGTGGCAAGC TTATC (SEQ ID NO:15) | |

TABLE 1-continued PCR primer pairs used in vector construction[a]

| Primer | Sequence[b] | Restriction site(s)[c] |
|---|---|---|
| Amplicon II | | |
| IR-R (U) | CGCTAGCgcttctact accccatcacc (6433–6453) (SEQ ID NO:16) | Eco47III |
| 1 (D) | gaagcggatgcgccaagg (7323–7340) (SEQ ID NO:18) | |

[a]The sequences of oligonucleotide primers used in two manipulations, duplication of the SG promoter in Robo302, and substitution of the SG promoter in Robo402/NsiI with an IRES from EMCV are given. In both manipulations, two PCR amplicons were generated and the manipulation was done via a three-fragment ligation. The upstream primer (U) sequence is at the 5' end of the amplicon with respect to the RUB genomic construct; the sequence of RUB nucleotides is thus colinear with the genomic sequence. The downstream primer (D) sequence is at the 3' end of the amplicon with respect to the RUB genomic construct; the sequence of RUB nucleotides is thus complementary with the genomic sequence.
[b]Nucleotides in the primers containing RUB sequences are underlined; those in the genome (numbered from the 5' end) to which the nucleotides in the primer are colinear or complementary are given in parentheses. NA, not applicable.
[c]Restriction site sequences in the primer used for cloning and the corresponding name are in bold. In the case of primer K3, used to create the MCS in dsRobo302, several restriction sites are present; they are alternately shown in bold and all italics.

EXAMPLE 7

Figure 5:
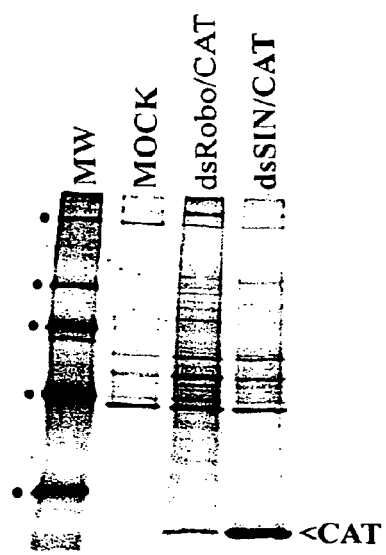
FIG. 5 is an autoradiograph showing an analysis by sodium dodecyl sulfate-polyacrylamide gel electrophoresis (SDS-PAGE) by the proteins that were immunoprecipitated by an anti-CAT monoclonal antibody from the protein extracts of the cells infected by dsRobo and SIN viruses. CAT expression is compared in the cells that were mock transfected (MOCK) or transfected with dsRobo302/CAT transcripts or transcripts from a double-subgenomic SIN vector expressing CAT, pTE5'2J/CAT (dsSIN/CAT). The molecular weight standards (MW) (from top to bottom) are 200, 97, 68, 43, and 29 kDa; CAT is marked.
Figure 6:
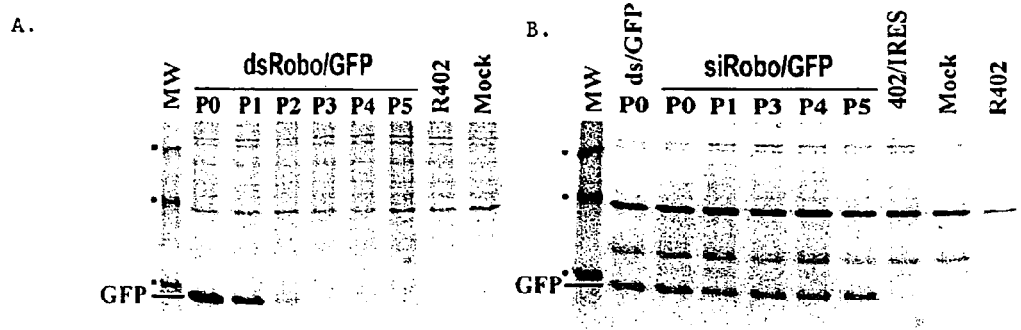
FIG. 6 is an autoradiograph showing analysis by SDS-PAGE of the proteins immunoprecipitated by an anti-GFP polyclonal antibody from the protein extracts of the cells infected by dsRobo (A) and siRobo (B) viruses. GFP expression is compared in Vero cells that were mock infected (Mock), infected with Robo402 virus (R402), Robo402/IRES virus (402/IRES), or a passaged stock of dsRobo/GFP or siRobo/GFP virus. In each panel, the three molecular weight standards (MW) are (from top to bottom) 68, 43, and 29 kDa; GFP is marked.
Figure 7:
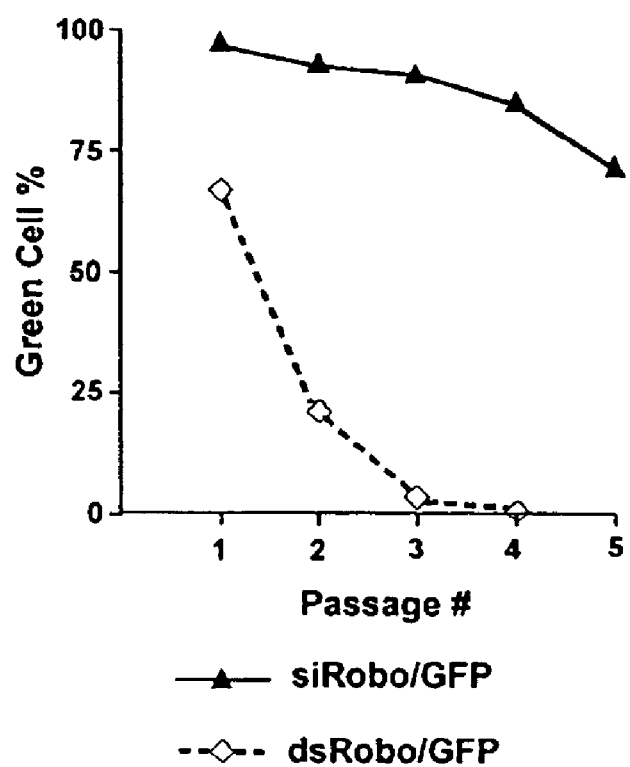
FIG. 7 is a graph showing percentage of cells in cultures infected with dsRobo/GFP and siRobo/GFP viruses expressing GFP. GFP-expressing cells were counted using fluorescence-activated cell sorting.
Figure 8:
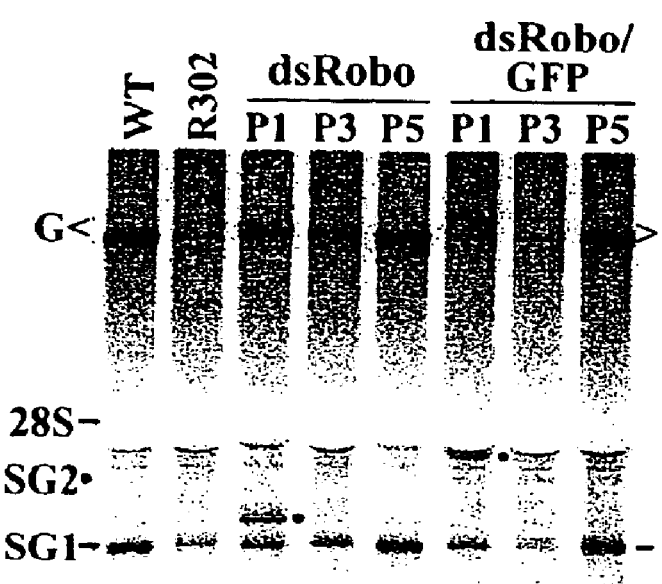
FIG. 8 is an autoradiograph showing the analysis by agarose gel-electrophoresis of virus-specific RNAs produced by dsRobo (panel A) and siRobo (panel B) constructs. RNAs are analyzed in Vero cells that were mock infected (Mock) or infected at an MOI of ~1 PFU/cell with Therien strain rubella (WT [wild type]), Robo302 or Robo402 virus (R302 or R402), or stocks of dsRobo, dsRobo/GFP, Robo402/IRES (402/IRES), or siRobo/GFP viruses passaged one (P1), three (P3), or five (P5) times in Vero cells (MOI of ~0.1 PFU/cell at each passage). In panel B, the dsRobo/GFP virus [ds/GFP] was P1). Marked are G, genomic RNA; 28S, the 28S cell rRNA which causes a background blob; SG1, the standard SG RNA; SG2, and SG RNAs engineered for expression of foreign genes. In the Robo402/IRES lanes, a faint band of unknown identity is marked with an arrowhead.
Figure 8:
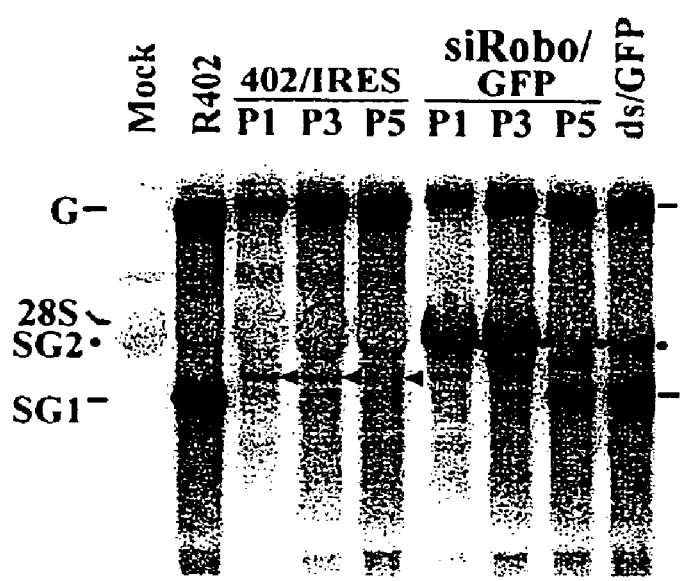

Testing of Expression of Chloramphenicol Acetyltransferase (CAT) from dsRobo302 Construct To test expression from dsRobo302, the reporter genes chloramphenicol acetyltransferase (CAT) was introduced into the multiple cloning site of dsRobo302. The resulting construct was termed dsRobo302/CAT. When in vitro transcripts from dsRobo302/CAT were used to transfect Vero cells, virus was recovered. As shown in FIG. 5, CAT expression was detected by both immunoprecipitation followed by sodium dodecyl sulfate-polyacrylamide gel electrophoresis (SDS-PAGE) and CAT enzyme assay using lysates from infected cells (described in 18, incorporated herein in its entirety by reference). Vero cells were mock transfected (MOCK) or transfected with dsRobo302/CAT transcripts or transcripts from a double-subgenomic SIN vector expressing CAT, pTE5'2J/CAT (dsSIN/CAT). The cells were metabolically radiolabeled with [$^{35}$S]methionine (1,000 Ci/mmol; Amersham) for 1.0 h at 25 (dsSIN/CAT) or 41 (MOCK and dsRobo/CAT) h posttransfection, followed by lysis with radioimmunoprecipitation buffer, immunoprecipitation using an anti-CAT monoclonal antibody (5'Prime-3'Prime, Inc.), and SDS-PAGE as described in Forng, R.-Y., et al., Virology 206:843–854 (1995). As shown in FIG. 5, CAT expression during a similar radiolabeling window from a corresponding SIN vector, pTE5'2J/CAT, was also assayed. Due to the growth differences and degree of cytopathic effect induced in infected cells, radiolabeling was done at 25 h posttransfection for the SIN vector and 41 h with the dsRobo vector. Predictably, expression was greater with the SIN vector, but expression with the dsRobo vector was readily detectable. When an enzyme assay (18) was used to quantitate the difference in expression using lysates prepared at the same times posttransfection, CAT expression by the SIN vector was approximately 7.5 times greater than CAT expression by the dsRobo vector. When lysates were prepared 4 and 6 days after transfection with dsRobo302/CAT, CAT expression increased 1.4- and 1.8-fold in comparison with the 2-day lysate.

EXAMPLE 8

Testing of Expression of Green Fluorescent Protein (GFP) from dsRobo302 Construct GFP was PCR amplified from SINrep/GFP plasmid (obtained from I. Frolov, currently and University of Texas Medical Center, Galveston, Tex.) with the primers that retained the initiation and termination codons of the GFP gene but added flanking XbaI and NsiI sites and cloned into the MCS of the dsRobo302 plasmid using these two enzymes. When in vitro transcripts from dsRobo302/GFP were used to transfect Vero cells, virus was recovered. GFP expression by the dsRobo vector was detected by examining living Vero cell cultures infected with dsRobo/GFP virus under a microscope with epifluorescence capability and by immunoprecipitation, as shown in FIG. 6. Vero cells were mock infected (Mock), or infected with Robo402 virus (R402) or a passaged stock of dsRobo/GFP virus. In these multiple passages, P0 is virus recovered from transfection which was subsequently passaged at a low MOI (~0.1 PFU/cell) to produce P1, P2, etc. For this experiment, the MOI for each virus stock was adjusted to ~1 PFU/cell. Three days postinfection, cells were metabolically radiolabeled with [$^{35}$S]methionine (1,000 Ci/mmol; Amersham) for 1.5 h followed by lysis with radioimmunoprecipitation buffer, immunoprecipitation using an anti-GFP polyclonal immunoglobulin G (Clontech), and SDS-PAGE, as described by Forng, R.-Y, et al., Virology 206:843–854 (1995). The percentage of cells in an infected culture expressing GFP was determined by flow cytometry, as shown in FIG. 4. Vero cells were infected at an MOI of 1 PFU/cell with dsRobo/GFP stocks produced by multiple low-MOI passages (virus recovered from transfected cells, designated P0, was passaged in Vero cells to produce P1, P2, etc.). Three to four days postinfection, when 100% of the cells are infected with Robo302 virus under these conditions, to determine the percentage of cells expressing GFP, the infected cultures were trypsinized, and the cells were resuspended in medium and subjected to fluorescence-activated cell sorting analysis using a Becton Dickinson FACS Calibur flow cytometer (equipped with a 388-nm, 16-mW argon laser) with CellQuest software (Becton Dickinson); 20,000 events were used to determine each percentage.

EXAMPLE 9

Properties of the dsRobo and dsRobo/GFP Viruses

The majority of plaques formed by P0 (passage 0, initial round of infection of cells by viruses) dsRobo and dsRobo/GFP virus (virus produced by transfected cultures) were smaller than Robo302 virus plaques; however, ~1% were similar in size to Robo302 virus plaques. P0 dsRobo and dsRobo/GFP virus titers were roughly $5\times10^5$ PFU/ml, in comparison to average P0 Robo302 virus titers of $5\times10^6$ PFU/ml. The analysis of intracellular RNA from infected cells is shown in FIG. 8. FIG. 8A shows analysis of intracellular viral RNA. Vero cells were mock infected (Mock) or infected at an MOI of ~1 PFU/cell with indicated strains of rubella viruses passaged one (P1), three (P3), or five (P5) times in Vero cells (MOI of ~0.1 PFU/cell at each passage) (in panel B, the dsRobo/GFP virus [ds/GFP] was P1). Three days postinfection, total cell RNA was extracted and subjected to agarose gel electrophoresis and virus-specific RNA species were detected by Northern hybridization using a probe complementary to the rubella SP-ORF ([$^{32}$P]CTP-labeled negative-polarity RNA transcripts synthesized from pRUB-SP-ORF, as described in Marr, et al., Virology 180:400–405 (1991). The amount of radioactivity present in RNA bands on autoradiographs was quantitated by densitometry with a Fujix BAS1000 Bio Imaging analyzer (Fuji Photo Film, Tokyo, Japan), using software provided by the manufacturer. The genomic RNAs of both dsRobo and dsRobo/GFP virus were larger than Robo302 virus genomic RNA, and both produced an additional, longer SG RNA not found in cells infected with Robo302 virus. The intensities of the two SG RNA bands relative to the genomic RNA were similar to each other and to the SG/genomic RNA ratio in Robo302 virus-infected cells, indicating that both SG promoters retained the functional efficiency found in standard virus. the results did add to our understanding of rubella replication strategy. The ability of dsRobo virus to synthesize two SG RNAs with equal efficiency demonstrates that the rubella SG promoter is somewhere within the duplicated region, i.e., 170 nucleotides upstream from the SG RNA start site. Among other applications, the dsRobo302/GFP construct will be of use in mapping the precise boundaries of the SG promoter.

EXAMPLE 10

Testing of Stability of dsRobo302/GFP Virus

When P0 dsRobo/GFP virus was passaged (multiplicity of infection [MOI] of 0.1 PFU/cell, with harvest at 5 to 6 days postinfection), the level of GFP expression diminished and was undetectable by radioimmunoprecipitation by P3, as shown in FIG. 6A. For this experiment, Vero cells were mock infected (Mock), or infected with Robo402 virus (R402)or a passaged stock of dsRobo/GFP virus. In these multiple passages, P0 is virus recovered from transfection which was subsequently passaged at a low MOI (~0.1 PFU/cell) to produce P1, P2, etc. For this experiment, the MOI for each virus stock was adjusted to ~1 PFU/cell. Three days postinfection, cells were metabolically radiolabeled with [$^{35}$S]methionine (1,000 Ci/mmol; Amersham) for 1.5 h followed by lysis with radioimmunoprecipitation buffer, immunoprecipitation using an anti-GFP polyclonal immunoglobulin G (Clontech), and SDS-PAGE (4). The percentage of cells in infected cultures expressing GFP declined precipitously through P3, and GFP-positive cells were not detectable in the fourth and subsequent passages, as shown in FIG. 7. Thus, GFP expression was unstable. FIG. 8A shows analysis of intracellular viral RNA. Vero cells were mock infected (Mock) or infected at an MOI of ~1 PFU/cell with Therien strain rubella (WT [wild type]), Robo302 virus (R302), or stocks of dsRobo or dsRobo/GFP passaged one (PI), three (P3), or five (P5) times in Vero cells (MOI of ~0.1 PFU/cell at each passage). Three days postinfection, total cell RNA was extracted and subjected to agarose gel electrophoresis and virus-specific RNA species were detected by Northern hybridization using a probe complementary to the rubella SP-ORF ([$^{32}$P]CTP-labeled negative-polarity RNA transcripts synthesized from pRUB-SP-ORF as described in Marr, et al., Virology 180:400–405 (1991). The amount of radioactivity present in RNA bands on autoradiographs was quantitated by densitometry with a Fujix BAS1000 Bio Imaging analyzer (Fuji Photo Film, Tokyo, Japan), using software provided by the manufacturer. The RNA analysis revealed that by P3, the dsRobo/GFP and similarly passaged dsRobo viruses synthesized no detectable second SG RNA, and the genomic RNA of these viruses was the same size as that of Robo302 virus. This suggests that GFP expression had been lost due to homologous recombination between the two SG promoters, which would restore the genomic RNA to the size of standard virus. Concomitant with loss of GFP expression, P2 and later-passage dsRobo and dsRobo/GFP virus produced plaques similar in size to Robo302 virus plaques.

EXAMPLE 11

Construction and Analysis of Robo404/IRES

To eliminate the possibility of homologous recombination in the rubella vector, it was investigated whether an IRES element could be incorporated into our rubella expression vector in place of the second SG promoter. Schematic map of the resulting Robo402/IRES vector is shown FIG. 4. First, Robo402 construct described in 12 was modified by the addition of an NsiI site immediately following the NSP-ORF to produce Robo402/NsiI. Then, a ~600-nucleotide amplicon containing the complete encephalomyocarditis virus internal ribosome entry site (IRES) was PCR amplified from pCEN plasmid (obtained from I. Frolov, currently at University of Texas Medical Center, Galveston, Tex.) using primers IR-5 and IR-3 (Table 1). This amplicon was rendered blunt ended with T4 DNA polymerase and then digested with NsiI. A second amplicon containing rubella sequence between the second codon of the SP-ORF and AscI (nucleotide 7313) was PCR amplified using primers IRES-R and 1 (Table 1). This amplicon was digested with Eco47III and AscI. The two amplicons were then combined in a three-fragment ligation with NsiI-AscI-digested Robo402/NsiI. Surprisingly, transcripts from this construct, Robo402/IRES, gave rise to viable virus which formed plaques on Vero cells. The average P0 titer of Robo402/IRES virus was 8.5×105 PFU/ml; the titer rose to 2.4×106 PFU/ml at P3 and 6.0×107 PFU/ml at P5. FIG. 5B shows the analysisis of RNAs produced by Robo402/IRES construct. Vero cells were mock infected (Mock) or infected at an MOI of ~1 PFU/cell with Therien strain rubella (WT [wild type]), Robo402 virus (R402), or stocks of Robo402/IRES (402/IRESpassaged one (P1), three (P3), or five (P5) times in Vero cells (MOI of ~0.1 PFU/cell at each passage). Three days postinfection, total cell RNA was extracted and subjected to agarose gel electrophoresis and virus-specific RNA species were detected by Northern hybridization using a probe complementary to the rubella SP-ORF ([$^{32}$P]CTP-labeled negative-polarity RNA transcripts synthesized from pRUB-SP-ORF, as described in Marr, et al., *Virology* 180:400–405 (1991). The amount of radioactivity present in RNA bands on autoradiographs was quantitated by densitometry with a Fujix BAS1000 Bio Imaging analyzer (Fuji Photo Film, Tokyo, Japan), using software provided by the manufacturer. In the Robo402/IRES lanes, a faint band of unknown identity is marked with an arrowhead. This analysis shows that the predominant virus-specific RNA species in Robo402/IRES virus-infected cells was the genomic RNA. A faint band of with a size slightly larger than that of the standard SG RNA was present. The ratio of the intensity of this band relative to the genomic RNA was 0.08 in P1 and declined to 0.006 and 0.003 in P3 and P5, respectively (in comparison, the SG/genomic intensity ratio was 1.2 in Robo402-infected cells). Therefore, although the identity of this band was not determined (for example, it could have been due to adventitious use of the IRES as an SG promoter), it is doubtful that it plays a significant role in Robo402/IRES virus replication. This analysis combined with the unexpected discovery that rubella was viable with an IRES element in place of its SG promoter shows for the first time that an IRES can drive the expression of structural genes in a togavirus in the absence of an SG RNA.

EXAMPLE 12

Construction of a siRobo402 Vector

A schematic map of a siRobo402 vector is shown in FIG. 4. To construct the siRobo402/GFP vector, the SG promoter followed by the GFP gene was introduced into Robo402/IRES. The BglII-NsiI fragment of dsRobo302/GFP was ligated into Robo402/IRES that had been restricted with these two enzymes. Virus produced from this construct should synthesize a single SG RNA; in this SG RNA, the GFP gene is 5' proximal and is followed by the IRES and the SP-ORF. A siRobo402 vector containing the dsRobo302 multiple cloning site between the SG promoter and the IRES element was created by similar introduction of the BglII-NsiI fragment from dsRobo402 into Robo402/IRES.

EXAMPLE 13

Analysis of Properties and Testing of Stability of siRobo402

Transcripts from siRobo402/GFP gave rise to virus following transfection of Vero cells. P0 titers of siRobo/GFP virus were $3\times10^4$ PFU/ml but rose to $4\times10^6$ PFU/ml at P3 and $1.2\times10^7$ PFU/ml at P5. GFP expression by siRobo/GFP virus assayed by immunoprecitpitation, as shown in FIG. 6B. Vero cells were mock infected (Mock), infected with Robo402 virus (R402), Robo402/IRES virus (402/IRES), or a passaged stock of dsRobo/GFP (ds/GFP) or siRobo/GFP virus. In these multiple passages, P0 is virus recovered from transfection which was subsequently passaged at a low MOI (~0.1 PFU/cell) to produce P1, P2, etc. For this experiment, the MOI for each virus stock was adjusted to ~1 PFU/cell. Three days postinfection, cells were metabolically radiolabeled with [$^{35}$S]methionine (1,000 Ci/mmol; Amersham) for 1.5 h followed by lysis with radioimmunoprecipitation buffer, immunoprecipitation using an anti-GFP polyclonal immunoglobulin G (Clontech), and SDS-PAGE (4). GFP expression by siRobo/GFP virus also analyzed by flow cytometry of infected cultures as shown in FIG. 4. Vero cells were infected at an MOI of 1 PFU/cell with siRobo/GFP stocks produced by multiple low-MOI passages (virus recovered from transfected cells, designated P0, was passaged in Vero cells to produce P1, P2, etc.). Three to four days postinfection, when 100% of the cells are infected with Robo302 virus under these conditions, to determine the percentage of cells expressing GFP, the infected cultures were trypsinized, and the cells were resuspended in medium and subjected to fluorescence-activated cell sorting analysis using a Becton Dickinson FACS Calibur flow cytometer (equipped with a 388-nm, 16-mW argon laser) with CellQuest software (Becton Dickinson); 20,000 events were used to determine each percentage. GFP expression by siRobo/GFP virus was relatively stable through P5 as assayed by both methods. P0 siRobo/GFP virus formed small opaque plaques, and this was the majority plaque morphology through P5, when ~10% of the plaques had Robo402 virus morphology. Analysis of intracellular virus-specific RNA produced by siRobo viruses is shown in FIG. 5B. Vero cells were mock infected (Mock) or infected at an MOI of ~1 PFU/cell with Therien strain rubella (WT [wild type]), Robo402 virus (R402), or stocks of dsRobo/GFP (dsGFP), Robo402/IRES (402/IRES), or siRobo/GFP viruses passaged one (P1), three (P3), or five (P5) times in Vero cells (MOI of ~0.1 PFU/cell at each passage). Except for dsRobo/GFP virus [ds/GFP], for which only P1 stock was tested. Three days postinfection, total cell RNA was extracted and subjected to agarose gel electrophoresis and virus-specific RNA species were detected by Northern hybridization using a probe complementary to the rubella SP-ORF ([$^{32}$P]CTP-labeled negative-polarity RNA transcripts synthesized from pRUB-SP-ORF, as described in Marr, et al., Virology 180:400–405 (1991). The amount of radioactivity present in RNA bands on autoradiographs was quantitated by densitometry with a Fujix BAS1000 Bio Imaging analyzer (Fuji Photo Film, Tokyo, Japan), using software provided by the manufacturer. This analysis revealed that the presence of the genomic RNA and an SG RNA larger than the standard SG RNA in P1 siRobo/GFP-infected cells, as expected. However, by P3, a band of intermediate size between the siRobo/GFP SG RNA and the standard SG RNA was present, and by P5 a band of similar in size to the standard SG RNA appeared. Concomitantly, a shorter genomic RNA band appeared with a size similar to the size of the standard genomic RNA. Thus, deletion events occurred during passage of siRobo/GFP virus, but at a much lower rate compared to dsRobo viruses. In FIG. 4B, it can be seen that GFP expression by siRobo/GFP virus declined to some extent in the passages during which these deletion events occurred. This result indicates that SG RNA synthesis was preferred. The siRobo vector exhibited greater stability of foreign expression than dsRobo. The strategy of using an IRES to increase stability of a rubella vector is also applicable to other togavirus, including alphavirus, vectors.

EXAMPLE 14

Expression of Immunogenic Viral Proteins in dsRobo and siRobo Rubella Expression Vectors and their Potential as Prototype Vaccine Candidates A truncated form of the immunogenic E proteins of Japanese encephalitis virus was expressed in both dsRobo and siRobo as prototype vaccine candidates. As rubella virus replicates in a variety of vertebrate cell types and in most of these replication is to low titers and without accompanying cytopathogenicity (unlike the Vero cells used in this study), one of the possible advantages of a rubella expression vector would be for low-level expression without a drastic effect on the cell, which has been a problem for the highly cytopathic alphavirus vectors described in prior art as described in Schlesinger, S., et al., *Curr. Opin. Biotechnol.* 10:434–439 (1999). A rubella-based vaccine would be useful in many settings, including but not limited to a pediatric setting to target systemic pathogens against which universal immunization was desired, such as human immunodeficiency virus, respiratory syncytial virus, or one of the hepatitis agents; a cocktail of rubella-based vaccines targeting different pathogens could be used to induce immunity simultaneously against each pathogen targeted in the cocktail.

All patents and publications mentioned herein are hereby incorporated by reference.

We claim:

1. A rubella virus expression vector, comprising a rubella virus non-structural protein open reading frame, a subgenomic promoter for expression of a foreign gene, operably linked to the foreign gene or a multiple cloning site for insertion of the foreign gene, and an internal ribosome entry site, operably linked to a rubella virus structural protein open reading frame.

2. The vector of claim 1, wherein the foreign gene is a heterologous virus gene.

3. The vector of claim 2, wherein the heterologous virus gene is an encephalitis virus gene, a hepatitis virus gene, or a Dengue fever virus gene.

4. The vector of claim 1, wherein the foreign gene is a reporter gene, wherein the reporter gene is a green fluorescent protein (GFP) gene, or a chloramphenicol acetyltransferase (CAT) gene.

5. A method of producing a rubella virus expression vector, comprising operably linking a rubella virus non-structural protein open reading frame, a subgenomic promoter for expression of a foreign gene, the foreign gene or a multiple cloning site for insertion of the foreign gene, an internal ribosome entry site for expression of a rubella virus structural protein open reading frame, and the rubella virus structural protein open reading frame.

* * * * *